(12) United States Patent
Leader et al.

(10) Patent No.: US 6,193,864 B1
(45) Date of Patent: Feb. 27, 2001

(54) LOCKING SENSOR CARTRIDGE WITH INTEGRAL FLUID PORTS, ELECTRICAL CONNECTIONS, AND PUMP TUBE

(75) Inventors: Matthew J. Leader, Laguna Niguel; Douglas R. Savage, Del Mar, both of CA (US)

(73) Assignee: SenDx Medical, Inc., Carlsbad, CA (US)

(*) Notice: Subject to any disclaimer, the term of this patent is extended or adjusted under 35 U.S.C. 154(b) by 0 days.

(21) Appl. No.: 09/184,471

(22) Filed: Nov. 2, 1998

Related U.S. Application Data

(63) Continuation-in-part of application No. PCT/US97/00773, filed on May 6, 1997, and a continuation-in-part of application No. 08/648,692, filed on May 16, 1996, now Pat. No. 5,718,816.

(51) Int. Cl.[7] .................................................. G01N 27/333
(52) U.S. Cl. ......................... 204/409; 204/400; 204/403; 204/416; 204/418; 205/775; 205/789.5
(58) Field of Search ..................................... 204/400, 403, 204/416, 418, 419, 409

(56) References Cited

U.S. PATENT DOCUMENTS

| | | | |
|---|---|---|---|
| 4,737,255 | * 4/1988 | Arruda et al. | 204/400 |
| 4,786,394 | 11/1988 | Enzer et al. | 304/401 |
| 5,230,785 | * 7/1993 | Yager | 204/400 |
| 5,571,396 | 11/1996 | Cormier et al. | 204/418 |
| 5,718,816 | * 2/1998 | Savage et al. | 204/400 |

FOREIGN PATENT DOCUMENTS

| | | | |
|---|---|---|---|
| 0 399 227 | 4/1990 | (EP) | G01N/33/48 |
| 0 579 997 | 7/1993 | (EP) | G01N/27/28 |
| 2076969 | * 12/1981 | (GB) . | |
| WO 95/02816 | * 1/1995 | (WO) . | |

* cited by examiner

Primary Examiner—T. Tung
(74) Attorney, Agent, or Firm—Baker & Maxham

(57) ABSTRACT

A blood analyzer sensor cartridge comprises a housing having chamber and a sensor assembly within the chamber, a first fluid port having an articulated inlet aspiration tube for direct introduction of a sample, a first fluid path in the housing communicating the first fluid port with the sensor assembly, a second fluid port in the housing adapted for connection to an analyzer, and a second fluid path in the housing communicating the sensor assembly with the second fluid port, the articulated tube is pivotally mounted to the housing for selective orientation within a range of up to ninety degrees, the tube is moveable from a protective recess in the housing to a position normal to a face of the housing.

20 Claims, 20 Drawing Sheets

LOCKING SENSOR CARTRIDGE WITH INTEGRAL FLUID PORTS, ELECTRICAL CONNECTIONS, AND PUMP TUBE

REFERENCE TO RELATED APPLICATIONS

This is a Continuation-in-part of PCT application Ser. No. PCT/US/97/0773 filed on May 6, 1997, and application Ser. No. 08/648,692 filed on May 16,1996, now U.S. Pat. No. 5,718,816.

BACKGROUND OF THE INVENTION

1. Field of the Invention

This invention relates to systems for analyzing fluids, and more particularly to an system for mechanical, electrical, and fluid interconnection of sensors to a blood analyzer.

2. Description of Related Art

In a variety of instances it is desirable to measure the partial pressure of blood gasses in a whole blood sample, concentrations of electrolytes in the blood sample, and the hematocrit value of the blood sample. For example, measuring $pCO_2$, $pO_2$, pH, $Na^+$, $K^+$, $Ca^{2+}$ and hematocrit value are primary clinical indications in assessing the condition of a medical patient. A number of different devices currently exist for making such measurements. Such devices are preferably very accurate in order to provide the most meaningful diagnostic information. In addition, in an attempt to perform these analyses in close proximity to the patent, the devices which are employed to analyze a blood sample are preferably relatively small. Furthermore, it is important to reduce the size of the cavities and pathways through which the analyte must flow in order to reduce the amount of analyte required. For example, performing blood analysis using a small blood sample is important when a relatively large number of samples must be taken in a relatively short amount of time. More particularly, patients in intensive care require a sampling frequency of 15–20 per day for blood gas and clinical chemistry measurements, leading to a potentially large loss of blood during patient assessment. Furthermore, the amount of blood available may be limited, such as in the case of samples taken from a neonate. In addition, by reducing the size of the analyzer sufficiently to make the unit portable, analysis can be performed at the point of care. Also, reduced size typically means reduced turnaround time. Furthermore, in order to limit the number of tests which must be performed it is desirable to gather as much information as possible upon completion of each test.

In one blood analyzer currently in use, a sensor/calibrant package comprises a sensor assembly mounted within a housing. The sensor/calibrant package also comprises a plurality of fluid pouches mounted within the housing. These pouches hold calibrants and flush fluids necessary for the operation of the blood analyzer. A series of tubes and valves within the housing interconnect the sensors within the sensor assembly to each of the fluid pouches. Since the tubes which transport a sample to the sensor assembly are within the housing, the operator of the blood analyzer can not see the sample as it flows into and out from the sensor assembly. Accordingly, the operator cannot determine visually whether the sample has entered the sensor assembly. This can be a significant problem, since the operator may not visually see that a blockage has occurred in the fluid flow path.

A heater assembly is mounted to the housing in order to raise the temperature of the fluids, the sensor assembly, and the sample to be measured. Raising the temperature allows the analysis of the sample to be carried out at a predetermined temperature. Due to the thermal mass of the components and fluids that must be heated, such blood analyzers may not be used for one or more hours after a new sensor/calibrant package has been installed. Furthermore, the need for such a heater substantially increases the cost of the sensor/calibrant package.

In addition to requiring that the sensor/calibrant package be heated, it is necessary to hydrate the sensors within the sensor assembly. Such hydration of the sensors takes one or more hours. Accordingly, the blood analyzer is not operational for one or more hours after installation of a new sensor assembly. In many cases analysis must be performed at regular and closely spaced intervals. Accordingly, if the heating and temperature stabilization time and the hydration time are relatively long, the number of times such analysis can be performed within a particular amount of time (i.e., turn around time) can be limited to a number less than would otherwise be desirable.

The fluid interface between the fluid pouches and the sensor assembly must be controlled to prevent fluid from pouches from flowing to the sensor assembly prior to installation of the sensor/calibrant package be installed in the blood analyzer. This requirement adds a measure of complexity to the mechanical design of the sensor/calibrant package, thus increasing the cost for fabricating the sensor/calibrant package. Furthermore, the complex interface between the sensor/calibrant package and the blood analyzer makes installation of the sensor/calibrant package more difficult, increases the chance that fluid will leak from the sensor, and can potentially increase the length of the fluid path (thus increasing the chance that a clot will occur and increasing the required volume of the sample). A portion of elastomeric tubing which interfaces the sensor assembly to the fluid pouches and a refuse pouch (into which exhausted samples and other fluids are pumped) is stretched over a concave surface. When the sensor/calibrant package is placed within the blood analyzer, a pump arm strokes the tubes in order to create a peristaltic pump, thus increasing the complexity of the mechanical interface between the sensor/calibrant package and the blood analyzer. Further complicating the mechanical interface is the need to provide a mechanism by which the blood analyzer can control the valves within the sensor/calibrant package. A first valve must be rotated to allow a controller within the blood analyzer to configure the fluid path. A set of additional slide valves must be actuated upon installation of the assembly into the blood analyzer in order to open the flow path from each of the fluid pouches.

The sensor assembly has a plurality of sensors formed on a front side of a polymeric substrate along a flow path between an inlet and outlet port. The fluid flow path is formed as a groove in a polymeric substrate. Electrodes are formed in the substrate. The electrodes communicate with a measurement flow channel formed in the substrate. The electrodes also communicate with a measurement flow channel which is formed by the combination of substrate and a cover plate.

The electrical interface between the sensor assembly and electronics external to the sensor assembly is provided through an plurality of contacts fabricated on the rear surface of the substrate. These contacts slide against a spring loaded mating contact in the blood analyzer. As the contacts of the sensor assembly slide against the mating contacts within the blood analyzer, the contacts of the sensor assembly and analyzer are worn down. Therefore, after inserting and removing the cartridge from the blood analyzer a number of times, the electrical connection between the external circuits within the blood analyzer and the sensors within the sensor assembly will be degraded.

Due to the use of electrical slide contacts, the structure of the interface between the elastomeric tubes and the pump, and the configuration of the valve controls, the sensor/calibrant package must first be inserted into the blood analyzer, and then slide generally at a right angle to the insertion angle. This process makes installation of the sensor/calibrant package awkward and increases the risk that either the electrical, mechanical, or fluid interface between the sensor/calibrant package and the blood analyzer will be faulty.

Furthermore, since the sensor is an integral part of the sensor/calibrant package, when a sensor fails (i.e., can no longer perform in accordance with specified parameters) the entire sensor/calibrant package must be replaced.

Accordingly, in as much as installation and fabrication of sensors within a blood analyzer are both cumbersome and susceptible to leaks, and long delays result after installation, it would be desirable to provide an assembly which allows the operator of a blood analyzer to replace merely the sensor assembly with a fast turn around time, no special training, and with highly reliable electrical, mechanical and fluid interface.

The aforementioned parent application solved many of the above enumerated problems of the prior art. However, a number of further improvements are desirable. For example, in the aforementioned system, the sample is introduced into the system through a port in the analyzer and passes through plumbing therein to the sensor cartridge. This has a number of disadvantages such as a longer fluid passage requiring a larger sample. The greater distance of travel of the sample also introduces a greater chance for contamination from gases and other materials.

Another problem is that the fluid passage in the analyzer becomes contaminated, not just from the blood but from calibrant materials which have salts in them.

Furthermore, it would be desirable to provide such an assembly which further allows the user to see a blood sample as it enters, flows through, and exits the sensor assembly.

SUMMARY OF THE INVENTION

The present invention is a sensor cartridge into which sensors are installed. The sensor cartridge allows the sensors to be easily and reliably installed into a blood analyzer. The cartridge includes six basic components: (1) a housing; (2) a housing cover; (3) a sensor assembly; (4) a "pump tube" assembly; (5) a right angle fluid coupling; and (6) a capture/release arm.

In accordance with the preferred embodiment present invention, the sensor assembly has an electrical connector mounted on the rear side of the assembly. The body of the connector protrudes through a first opening in the housing. The walls of the first opening conform generally to the profile of the protruding body of the connector. Thus, the mechanical interface between the body of the connector and the walls of the first opening in the housing retain the sensor assembly in a predetermined position within the housing.

A plurality of inner walls within the housing locate the pump tube assembly and the right angle fluid coupling within the housing. One end of the pump tube assembly is formed as a straight end fluid coupling and is coupled to the sensor assembly. The other end of the pump tube assembly is formed as a right angle end fluid coupling. A portion of the right angle end fluid coupling protrudes through a second opening in the housing. The walls which define the second opening conform to that portion of the right angle end fluid coupling which protrudes through the housing. The right angle fluid coupling is essentially similar to the right angle end fluid coupling of the pump tube assembly. A portion of the right angle fluid coupling protrudes through a third opening in the housing in a manner similar to the protrusion of the right angle end fluid coupling of the pump tube assembly. Another portion of the right angle fluid coupling is coupled directly to the sensor assembly.

In accordance with one embodiment of the present invention, a fourth opening in the housing receives a first boss which extends from the blood analyzer. The first boss is generally cylindrical and solid with a "ring-like" groove machined near the distal end of the boss. Alternatively, the boss may be formed as an elongated structure having a rectangular, oval, or other cross-section. In accordance with this embodiment, a second boss is formed in the housing as a hollowed cylinder having an inner diameter which is nearly equal, but slightly larger than the outer diameter of the first boss. The outer diameter of the second boss is greater than the inner diameter by an amount which is essentially equal to the thickness of the housing walls.

The capture/release arm has an opening through which the first boss protrudes. The arm is resiliently held in place such that an inner edge of the opening is captured within the ring-like groove in the boss that extends from the blood analyzer when the cartridge is installed in the blood analyzer. A portion of the arm extends beyond the housing to allow an operator to press the arm and thus release the edge of the arm from the groove in the boss.

Electrical contacts of the connector on the rear side of the sensor assembly are aligned to mating electrical contacts of the blood analyzer as the sensor assembly is being installed by alignment of the boss which extends from the blood analyzer to mate with the boss which extends from the housing, and alignment of two male fluid connectors, one of which mates with the right angle fluid coupling and the other of which mates with the right angle end fluid coupling of the pump tube assembly. Each of these will engage with the mating member prior to the electrical contacts of the sensor assembly engaging the electrical contacts of the blood analyzer. Accordingly, the electrical contacts of the sensor assembly will be in close alignment with the electrical contacts of the blood analyzer as the contacts approach one another.

A resilient portion of the pump tube assembly exits the housing at one end and re-enters the housing at the same end, forming a "U" shaped loop. The loop formed by the pump tube is sufficiently flexible and resilient to allow the loop to be stretched over and into engagement with a roller pump located on the blood analyzer. The roller pump rotates to massage the loop of the pump tube with which the roller pump is engaged in order to form a peristaltic pump.

In accordance with the preferred embodiment of the present invention, a heater is disposed within the substrate. The heater is capable of heating a blood sample and the array of sensors to a known stable temperature and maintaining that temperature as the sample is being analyzed. Accordingly, fluids that enter the sensor assembly are rapidly heated due to the small volume and low thermal mass of such fluids.

The sensors of the present invention have very good signal to noise ratio due to a short electrical path length between the sensors and external detecting and analyzing electronics within the blood analyzer. Thus, unamplified, low level sensor outputs from the sensors can be used directly.

BRIEF DESCRIPTION OF THE DRAWINGS

The objects, advantages, and features of this invention will become readily apparent in view of the following description, when read in conjunction with the accompanying drawings, in which:

FIGS. 3a1–3a2 is an illustration of a latch used to mechanically secure a cartridge to a blood analyzer in accordance with one embodiment of the present invention.

FIGS. 3b1–3b2 is an illustration of a protective cover in accordance with one embodiment of the present invention.

Like reference numbers and designations in the various drawings refer to like elements.

DETAILED DESCRIPTION OF THE INVENTION

Throughout this description, the preferred embodiment and examples shown should be considered as exemplars, rather than limitations on the present invention.

Sensor Cartridge

Figure 1A:
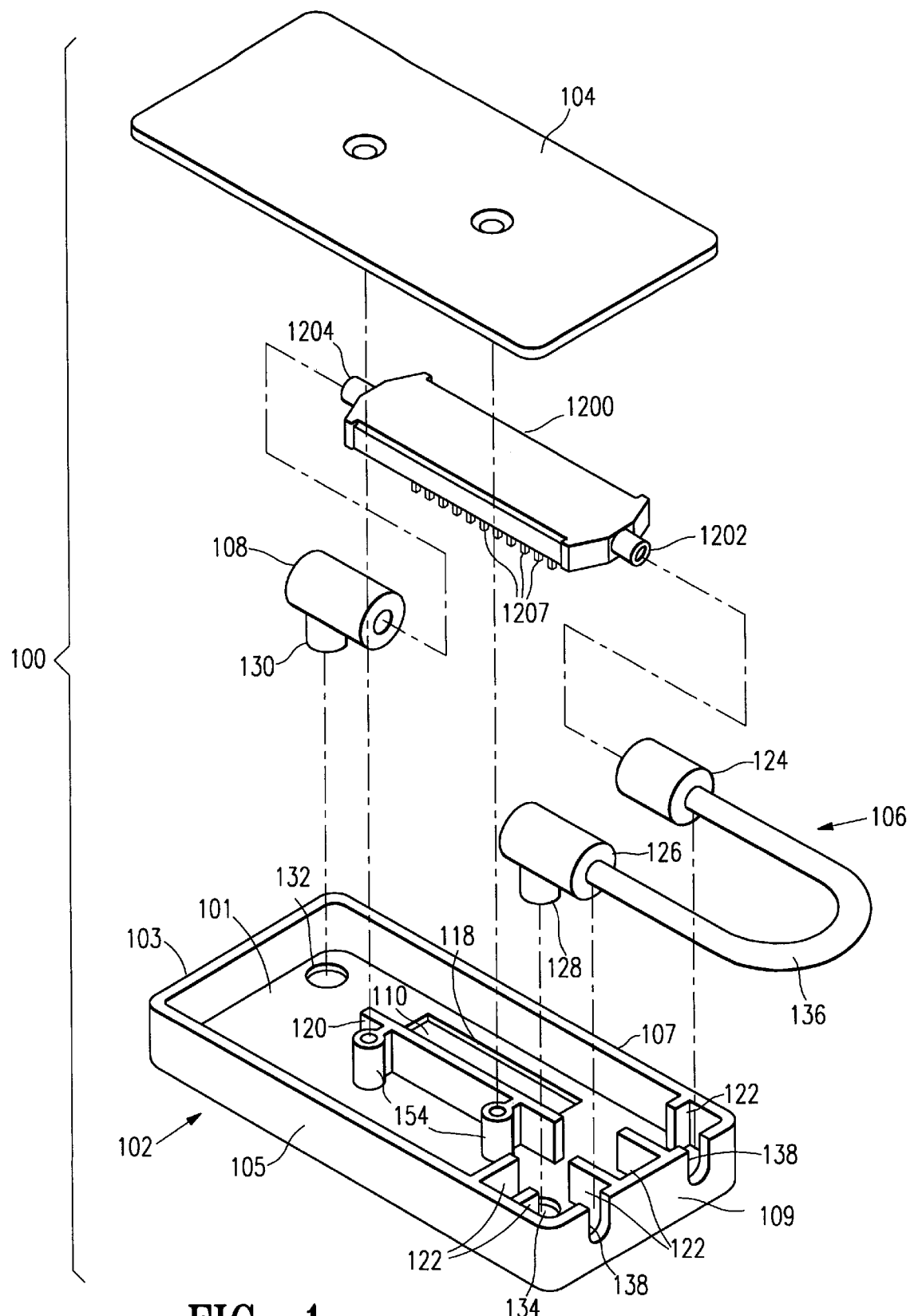
FIGS. 1a and 1b are perspective views of a disassembled sensor cartridge in accordance with one embodiment of the present invention.
Figure 1B:
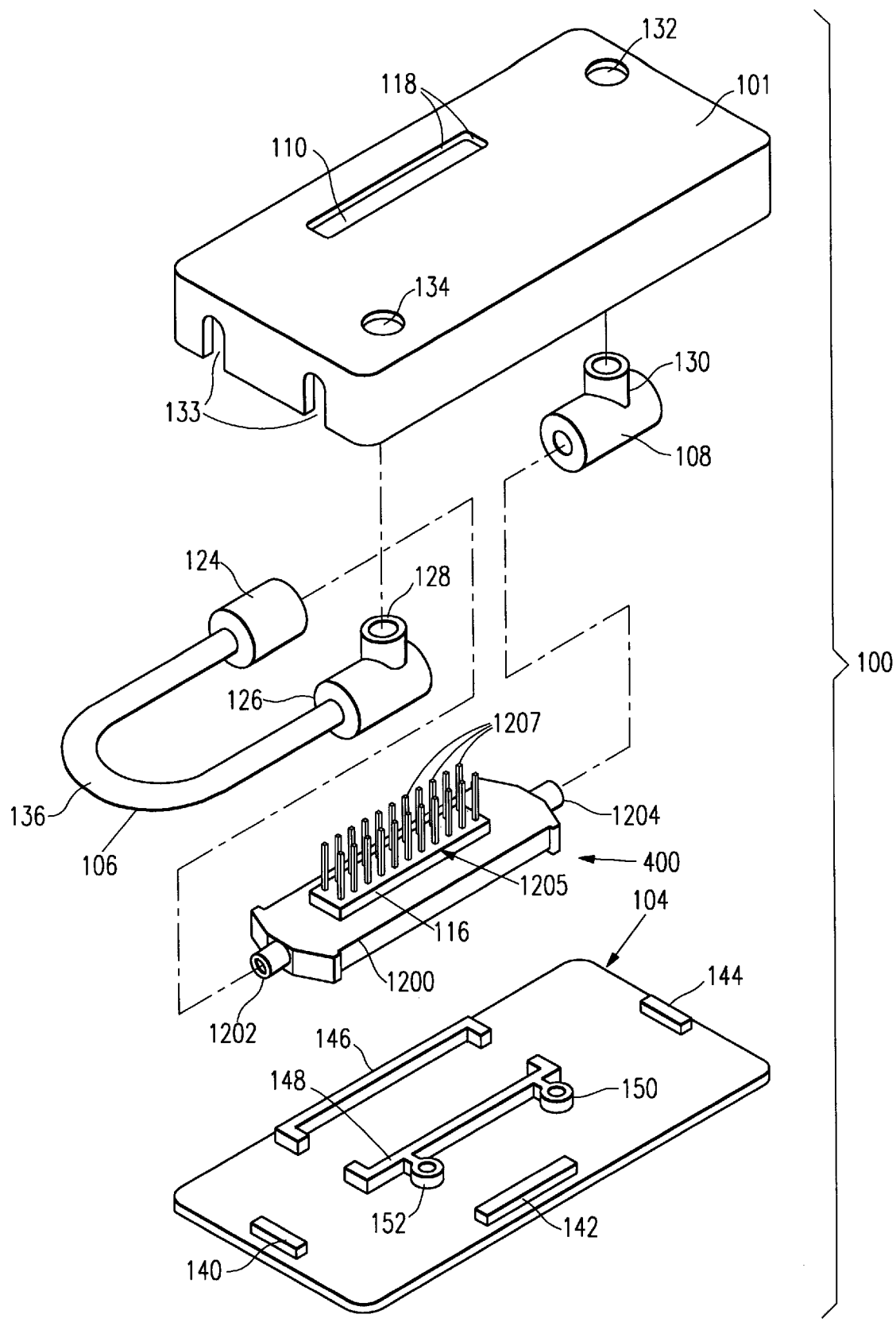

FIGS. 1a and 1b are perspective views of a disassembled sensor cartridge 100 in accordance with one embodiment of the present invention. The sensor cartridge 100 shown in FIGS. 1a and 1b has five component parts; (1) a housing 102; (2) a housing cover 104; (3) a pump tube assembly 106; (4) a fluid coupling 108; and (5) a sensor assembly 400.

The housing 102 shown in FIGS. 1a and 1b has a floor 101, four walls 103, 105, 107, 109, and an opening 110. Male electrical contact pins 1207 of an electrical connector 1205 of the sensor assembly 400 protrude through the opening 110. In accordance with one embodiment, the connector 1205 has a body 116 which also protrudes through the opening 110. The walls 118 of the opening 110 generally conform to the shape and size of the body 116 of the connector 1205. Thus, the sensor assembly 400 is constrained from movement in the plane of the floor 101 of the housing 102. Preferably, the connector body 116 fits loosely within the opening 110. However, in one alternative embodiment of the present invention, the body 116 may be friction fit within the opening 116 to more securely hold the sensor assembly in place during assembly of the cartridge 100. Alternatively, the sensor assembly may be held in place merely by the forces exerted by the fluid coupling of the sensor assembly 400 to the pump tube assembly 106 and the fluid coupling 108. In yet another alternative embodiment, walls which extend up from the floor 101 of the housing 102 may be formed to constrain any motion of the sensor assembly 400. FIG. 1a shows one such wall 120.

The pump tube assembly 106 preferably comprises a right angle end fluid coupling 126, a straight end fluid coupling 124, and a pump tube 136. In accordance with one embodiment of the present invention, the end fluid couplings 124, 126 are formed (such as by a conventional molding process) from an elastomer. The fluid coupling 108 may also be formed from an elastomer. The fluid coupling 108 is preferably formed as a right angle coupling. That is, the coupling provides a means by which a fluid flow path through a first mating fluid coupling may be placed in fluid connection with a fluid flow path through a second mating fluid coupling when the fluid flow paths of the first and second coupling are at right angles to one another. The pump tube 136 is preferably very resilient in order to allow the pump tube 136 to properly interface with a roller to form a peristaltic roller pump, as is described below in greater detail. A fluid path is formed through the pump tube assembly 106 such that fluid enters at one end of the pump tube assembly and exits from the other end.

Figure 1C:
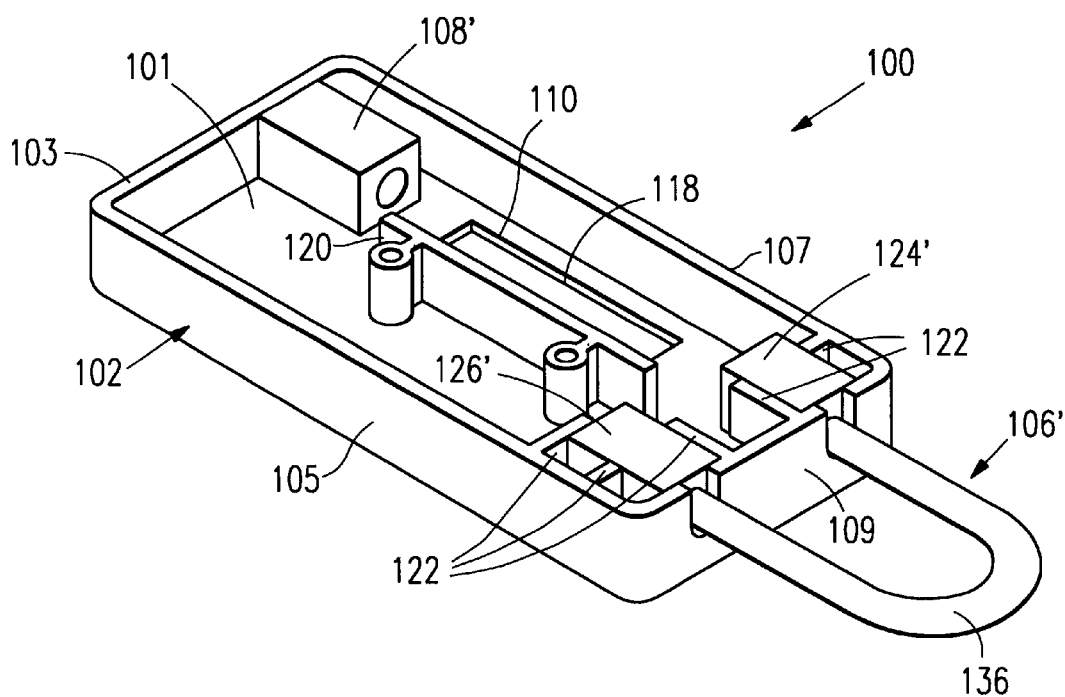
FIG. 1c illustrates one embodiment of the housing of the present invention with a pump tube assembly and a right angle fluid coupling installed within the housing.

Walls 122 may be provided to retain the pump tube assembly 106 and fluid coupling 108 in position within the housing 102. FIG. 1c illustrates one embodiment of the housing 102 of the present invention with a pump tube assembly 106' and a fluid coupling 108' installed within the housing 102. It can be seen that FIG. 1c shows an alternative to the embodiment shown in FIG. 1a and 1b, in that the end fluid coupling 124', the right angle end fluid coupling 126', and the fluid coupling 108' shown in FIG. 1c are generally rectangular (in contrast with the generally cylindrical shapes shown for the end fluid coupling 124, the right angle end fluid coupling 126, and the fluid coupling 108 shown in FIG. 1a and 1b). Hollow cylindrical protrusions from the body of the couplings 108, 108', 126, 126' have fluid channels therethrough. The fluid channel in each coupling 108, 108', 126, 126' is at a right angle to a fluid channel along the longitudinal axis of the each coupling 108, 108', 126, 126'. Regardless of the shape of the couplings, the protrusions 130, 128 are seated in two openings 132, 134 in the floor 101 of the housing 102 (best seen in FIGS. 1a and 1b). Preferably, the openings are shaped and sized such that the cylindrical protrusions 128, 130 fit snugly within the openings 132, 134 and extend just beyond the outer surface of the floor 101. In either case, a pump tube 136 of the pump tube assembly 106, 106' passes through openings 138 in the housing wall 109.

In accordance with one embodiment of the present invention, ports 1202, 1204 of the sensor assembly are directly coupled to the pump tube assembly 106 and the fluid coupling 108. However, in an alternative embodiment, an extension tube (not shown) with a fluid channel therethrough may be provided between the inlet port 1202 and the fluid coupling 124 or between the outlet port 1204 and the fluid coupling 108. The fluid channel through the extension tube is preferably relatively narrow to reduce the volume of the sample being analyzed and the amount of calibrant and other fluids used during analysis.

The cover 104 is preferably translucent or clear and has five protrusions 140, 142, 144, 146, 148 which extend upward from the surface of the cover 104. Furthermore, as will be described in greater detail below, a plastic encasement 1200 (see FIG. 14) is also preferably either translucent or clear. Since the cover and the plastic encasement are either translucent or clear, the user can view the movement of analytes gas bubbles, and reagents through the sensor assembly within the cartridge. In accordance with one embodiment of the present invention, illustrated in FIG. 1e, the cover 104' has an opening 170 which allows the user of a blood analyzer into which the cartridge is to be installed to view the sensor assembly directly. Accordingly, the user may directly observe an analyte gas bubbles and reagents flowing through the sensor assembly.

In one embodiment of the present invention, the protrusions 140, 142, 144, 146 align the cover 104 to the housing 102. The protrusion 146 also applies pressure to the top of the sensor assembly 400, together with the protrusion 148, in order to retain the sensor assembly in position after the cover 104 is applied. It will be understood by those skilled in the art that the protrusions may be formed in a wide variety of shapes in order to align the cover and retain the sensor assembly 400 in place. Furthermore, in one embodiment of the present invention, no such protrusions are provided.

Two reinforced holes 150, 152 are provided through the cover 104. The holes 150, 152 align with two hollow generally cylindrical bosses 154 which extend up from the floor 101 of the housing 102 to accept retaining devices, such as screws, which secure the cover 104 to the housing 102. In an alternative embodiment of the present invention, studs extend from the cover in alignment with the bosses 154. Each stud fits tightly within the opening in one of the bosses 154 in order to secure the cover 104 to the floor 101 of housing 102.

In accordance with one embodiment of the present invention, the cartridge of the present invention is assembled by coupling the fluid coupling 108 to a first port 1204 of the sensor assembly 400. The fluid coupling 124 is coupled to the other port 1202 of the sensor assembly 400. The combination of fluid coupling 108, sensor assembly 400, and pump tube assembly 106 are then lowered into the housing 102 and the protrusions 128, 130 are inserted into the openings 132, 134. The pump tube 136 is inserted into openings 138 in the wall 109 of the housing 102. The cover 104 is then placed over, and secured to, the housing 102.

Figure 2A:
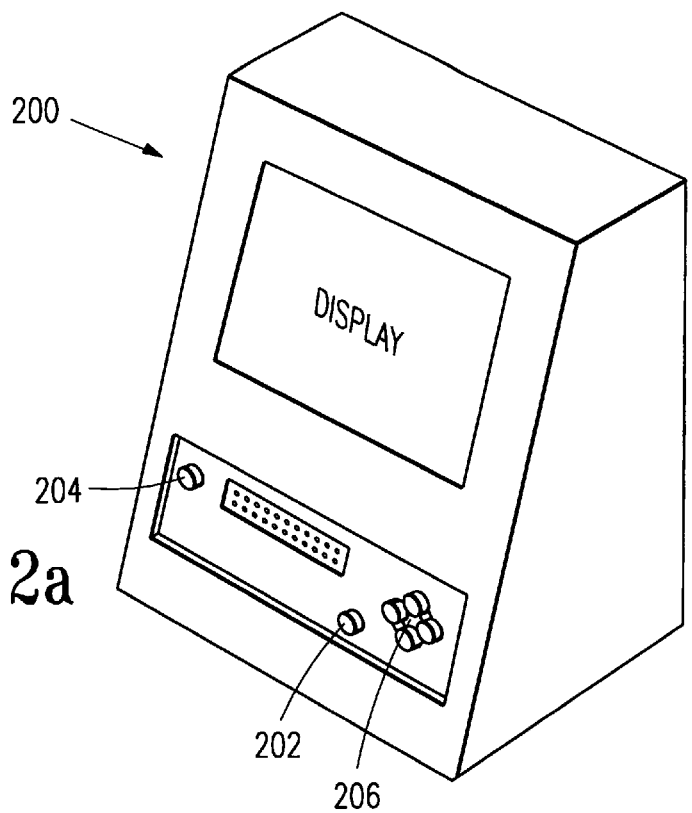
FIG. 2a is an illustration of a blood analyzer in accordance with one embodiment of the present invention.

Once the cartridge 100 is assembled, it may be installed in a blood analyzer, such as the blood analyzer 200 illustrated in FIG. 2a. The blood analyzer of the present invention has a first and second male fluid connector 202, 204 respectively. The first and second male fluid connectors mate with the cylindrical protrusions 128 and 130 to complete a fluid flow path from the first male fluid connector 202, through the right angle end fluid coupling 126 of the pump tube assembly 106, into the sensor assembly 400, through the inlet port 1202, out the outlet port 1204, through the fluid coupling 108, and into the second male fluid connector 204.

Fluids are pumped along the fluid flow path by a peristaltic roller pump which includes a roller 206 that massages the pump tube 136. That is, the pump tube 136 is preferably resilient enough to be stretched over the roller 206. The roller 206 applies areas of alternating greater and lesser pressure to the pump tube 136, causing those portions of the pump tube 136 that lie over an area of greater pressure to be internally constricted and those areas of the pump tube 136 that lie over an area of lesser pressure to be relaxed to essentially the full unstressed diameter of the channel through the interior of the pump tube 136. As the roller 206 rotates, the areas of alternating greater and lesser pressure traverse the pump tube 136 to generate a peristaltic action in the pump tube 136.

Figure 2B:
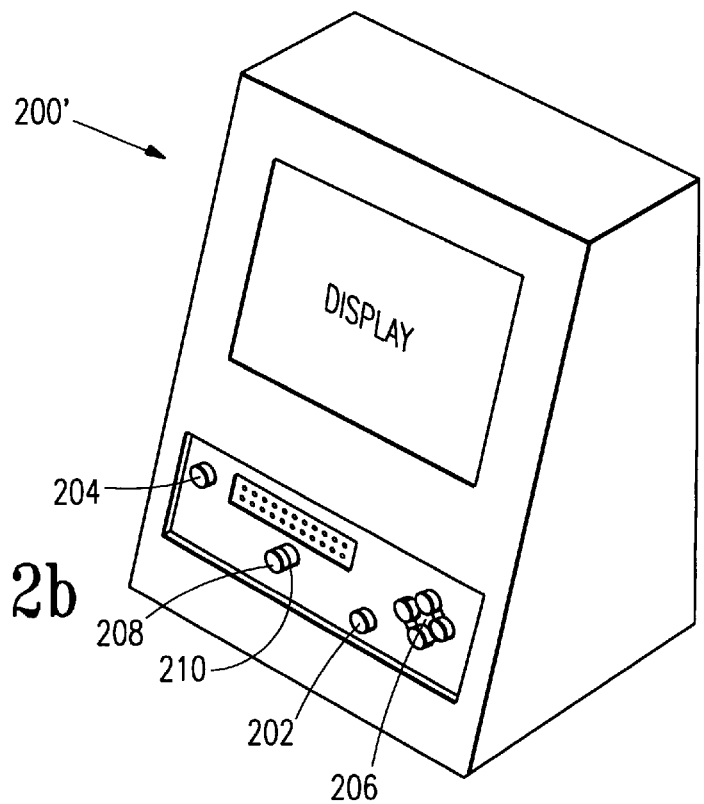
FIG. 2b is an illustration of another embodiment of a blood analyzer in accordance with the present invention.

In addition to the first and second male fluid connectors 202, 204, a female electrical connector having a plurality of female electrical contact receptacles are provided on the blood analyzer. The female receptacles mate with the male electrical contact pins 1207 of the sensor assembly 400. The first and second male fluid connectors 202, 204 preferably extend out further from the blood analyzer than do male electrical contact pins from the sensor assembly. Accordingly, the mating of the fluid connectors causes the electrical connectors to align for mating. In one embodiment of the present invention shown in FIG. 2b, a generally cylindrical boss 208 extends outward from the blood analyzer 200'. The boss 208 preferably has a generally ring-shaped groove 210 disposed near the distal end of the boss 208.

Figure 1D:
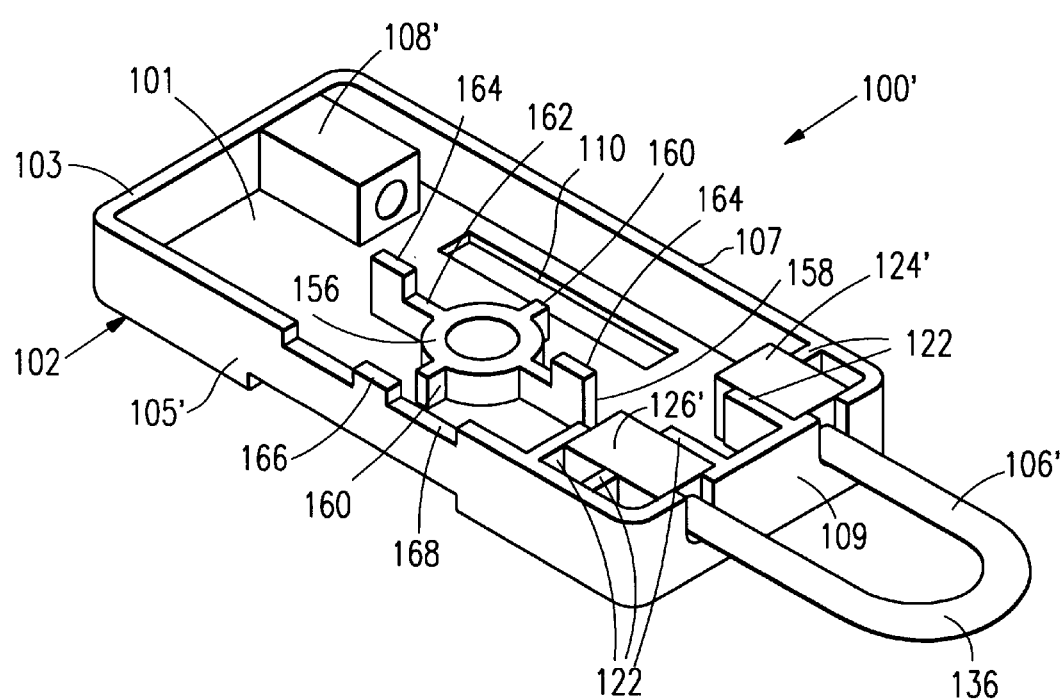
FIG. 1d illustrates a cartridge in accordance with one embodiment of the present invention in which a boss protruding from a blood analyzer mates with a hollow boss in the cartridge.
Figure 1E:
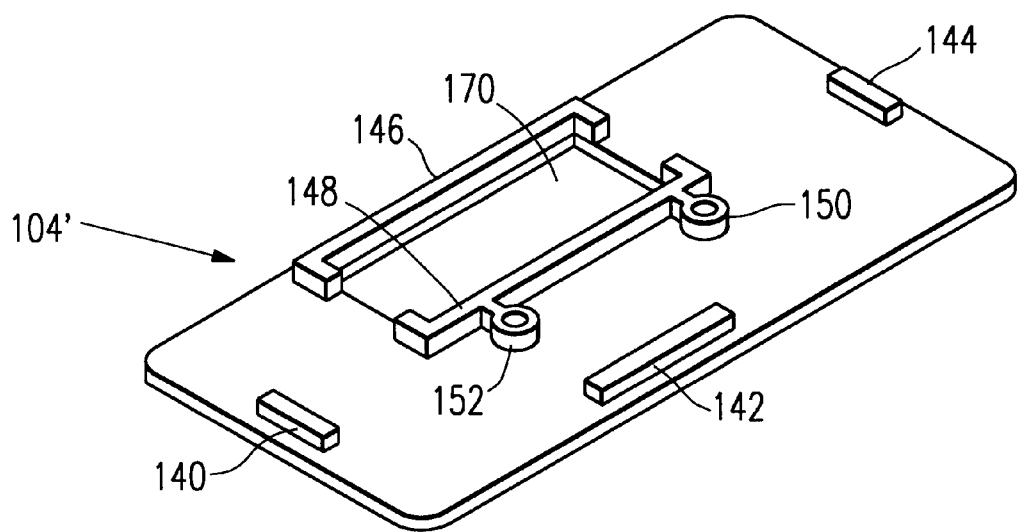
FIG. 1e is an illustration of the cartridge cover having an opening through which a sensor assembly can be viewed in accordance with one embodiment of the present invention.

In accordance with one embodiment of the present invention, a blood analyzer 200 FIG. 2D is provided with a boss 208. A cartridge 100' such as shown in FIG. 1d is provided. The cartridge 100' has an hollow boss 156 located in alignment with the boss 208. The hollow boss 156 of the cartridge has an inner diameter which is slightly larger than the outer diameter of the boss 208. Four support projections are provided around the periphery of the boss 156. Two of the support projections form generally "L-shaped" latch supports 158. The other two supports 160 merely provide additional strength to support the boss 156. FIG. 3a is an illustration of a latch 300 which rests on the horizontal edge 162 of each latch support 158 and between the upright portions 164 of each latch support 158.

A first smaller opening 301 is formed near a proximal end of the latch 300. A second larger opening 302 in the latch 300 is sized such that the boss 208 may pass though the second opening 302. At one end of the second opening a step 304 is formed. The first opening is sized to accept a "tooth" 166 which projects upward from a depressed portion 168 of the wall 105', as shown in FIG. 1d. The wall 105' is cut away from the floor 101 of the housing 102 in order to allow that portion of the wall 105' which is under the tooth 166 to flex inward. Thus, when the latch 300 is in position between the upright portions 164 of the latch supports 158 with the tooth 166 engaged with the opening 301, the latch may be urged inward by applying an inward pressure to the edge 306 of the latch 300 which will protrude from the wall 105'. When the cartridge 100' is completely assembled, the cover 104 retains the latch 300 in position.

When the cartridge 100' is installed in the blood analyzer 200', the groove 210 in the boss 208 engages the step 304 in the latch 300. That is, the distance between the edge of the first opening 301 in the latch and the edge of the step 304 is equal to the distance between the inner edge of the tooth 166 and the furthest point of the inner wall of the boss 156 minus the depth of the groove 210 in the boss 208. The width "w" of the step 304 is preferably at least equal to the depth of the groove 210. Furthermore, the thickness of the step "t" is slightly less than the width of the groove 210. Thus, the cartridge 100' is captured in the blood analyzer by the engagement of the step 304 in the groove 210. By applying inward pressure to the edge 306 of the latch 300, the latch will move slightly inward as the wall 105' flexes, thus releasing the step 304 from the groove and allowing the cartridge 100' to be removed from the blood analyzer 200'. It can be seen that all of the connections between the blood analyzer and the cartridge are preferably made by moving the cartridge in one direction along a straight line toward the blood analyzer. Upon proper engagement between the blood analyzer and the cartridge, the latch 300 snaps into position, providing a positive audible response to indicate that proper engagement has been achieved.

In accordance with one embodiment of the present invention, a protective cover is provided which generally conforms to the shape of the cartridge 100. FIG. 3b1–3b2 is an illustration of one such cover. Plugs 350 protrude from the cover 352. The plugs 350 are sized to engage the protrusions 128, 130 in the couplings 108, 126 in order to seal the couplings when the cartridge is not installed in a blood analyzer. Preferably, each plug 350 fits snugly within the channel through one of the protrusions 128, 130. A portion 354 of the cover is extends outward from the cover 354 to support the pump tube 136. A pair of walls 356 prevent the cartridge from seating too deeply into the cover 352 and thus prevent the contacts of the electrical connector 1205 from contacting the bottom of the cover 352. The cover 352 thus seals the fluid path through the sensor cartridge and covers and protects the electrical contacts of the sensor assembly 400.

It can be seen from the above description of the cartridge that the present invention provides a cartridge that: (1) is very easy to install, and thus may be installed with virtually no training; (2) establishes both electrical and fluid connections in one installation process with little or no risk of misaligning the electrical or fluid connections of the cartridge with the corresponding connections of the blood analyzer; (3) includes an integral inexpensive and reliable pump tube assembly; (4) allows the user of the blood analyzer to see the movement of an analyte, gas bubbles, or reagent during analysis; (5) is inexpensive and thus may be disposed of without concern for excessive cost; (6) facilitates rapid, reliable replacement of the sensors of the blood analyzer; (7) reduces contact between blood elements and the analyzer; (8) is compact in size; (9) can be used for sensors with different analyte panels; and (10) allows one type of analyzer to accept many different types of sensors.

Figure 3C:
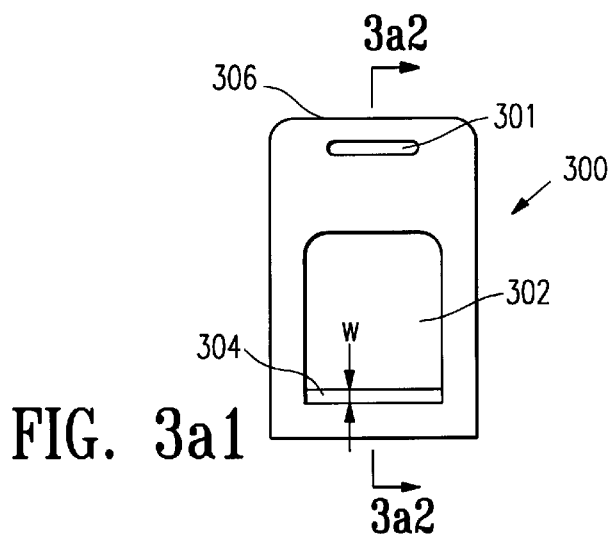
FIG. 3c is an illustration of one embodiment of the present invention in which barbs extending from a blood analyzer latch a sensor cartridge into place.
Figure 3C:
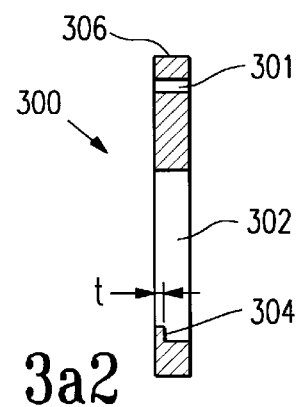
Figure 3C:
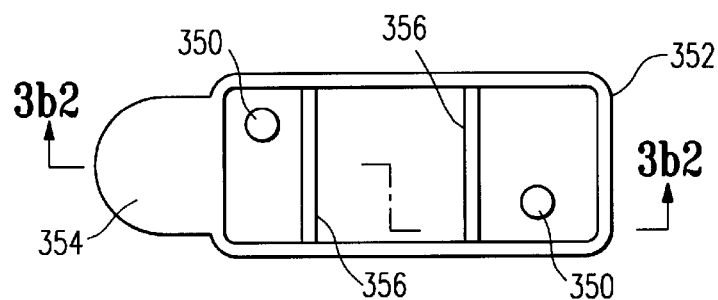
Figure 3C:
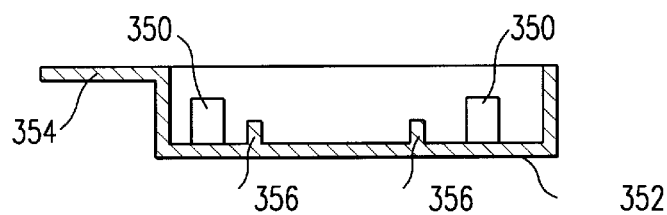
Figure 3C:
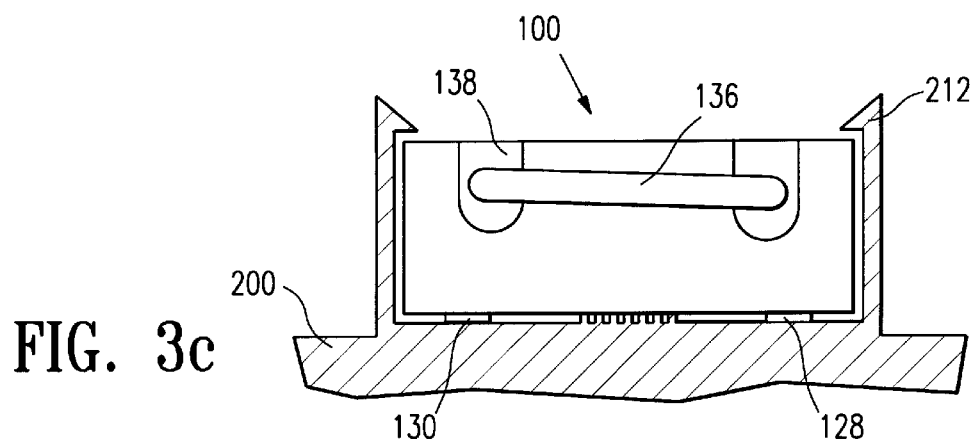

It should be understood that the cartridge of the present invention may be provided in numerous alternative configurations. For example, a plurality of sensor assemblies may be coupled in series to provide redundancy or to increase the number or type of sensors that are provided within the cartridge. Furthermore, straight fluid couplings may replace the right angle fluid couplings, and flexible tubing may be used to alter the direction of the flow path. Furthermore, the pump tubing may be directly coupled to the sensor assembly without the need for a fluid coupling between the pump tubing and the sensor assembly. Furthermore, a wide variety of latching mechanisms may be used to securely latch the cartridge to a blood analyzer. For example, the analyzer may have resilient barbs. FIG. 3c is an illustration of one embodiment in which barbs 212 spread apart as each edge of a cartridge 100 engages one of the barbs 212. Upon completely installing the cartridge 100, the barbs 212 then return to essentially the same position as they maintain without the cartridge with the barbed ends latching the outer surface of the cover of the cartridge. Furthermore, a resilient strap may be stretched across the cartridge to retain the cartridge in engagement with the analyzer 200. Still further, a hole through the cartridge may be provided to allow a threaded member to engage a tapped hole in the analyzer, thus securing the cartridge to the analyzer. It will be clear that numerous other alternatives are possible.

Sensor Assembly

Figure 4:
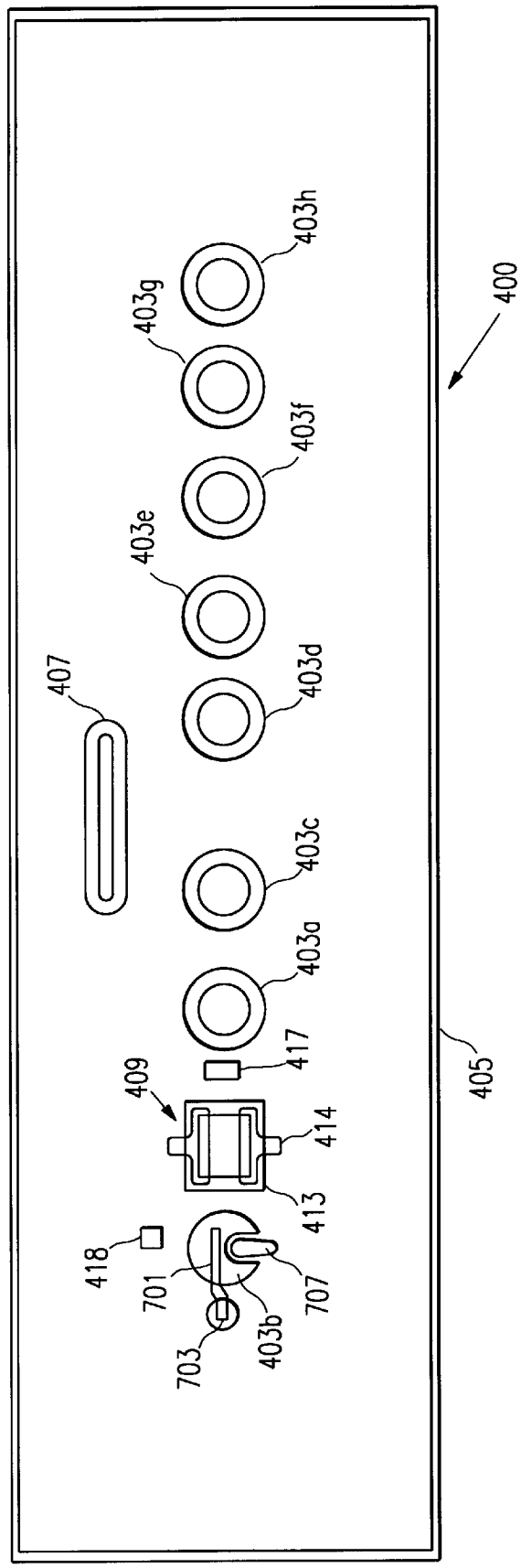
FIG. 4 is a front plan view of the sensor assembly of the present invention.
Figure 5:
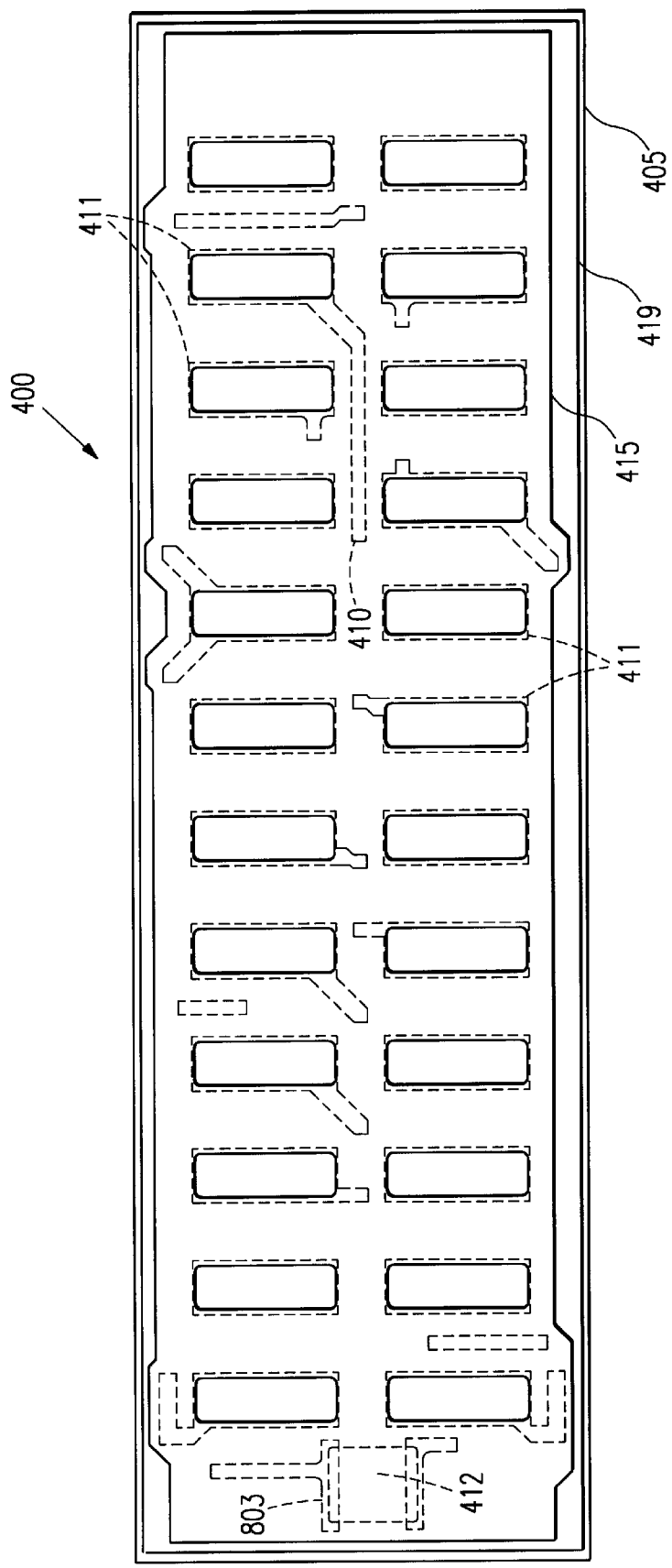
FIG. 5 is a back plan view of the sensor assembly of the present invention shown in FIG. 4.

FIG. 4 is a front plan view of one embodiment of the sensor assembly 400 of the present invention. FIG. 5 is a back plan view of the sensor assembly 400 of the present invention shown in FIG. 4. The present invention is a sensor assembly 400 having a plurality of sensors 403, including highly pure, planar circular silver potentiometric and amperometric electrode sensors disposed on an inorganic substrate 405. The sensor assembly 400 is preferably enclosed within a housing which defines a flow cell into which an analyte is transferred for analysis by the sensors 403. Each sensor 403 is fabricated over a subminiature through hole through the substrate 405. In accordance with the preferred embodiment of the present invention, each subminiature through hole is preferably laser drilled through the substrate. These through holes reduce the amount of area required on the front side of the substrate by each of the sensors 403. That is, the present design geometry permits a number of sensors to be arrayed in a plane with fewer restrictions, since the layers of the conductors do not interfere with the placement of the sensor electrodes. Reducing the required area on the front side of the substrate allows a relatively large number of sensors 403 to be located in a relatively small area on the sensor assembly 400, and thus allows the volume of the flow cell to be reduced. Reducing the volume of the flow cell reduces the sample size, which is important, since in some situations many samples are required from the same patient. Furthermore, as a consequence of the small sample size, the low thermal mass of the sensor assembly 400, and the placement of a heater on the back side of the substrate, the present invention rapidly reaches a stable temperature at which analysis can be performed. Accordingly, the present invention can be installed into a blood analyzer (not shown) to provide rapid results (i.e., approximately 60 seconds in the case of one embodiment).

In addition to reducing the area required for each sensor 403, the use of subminiature through holes through the substrate under each sensor 403 allows the sample and reference solution to be physically isolated by the substrate 405 from the electrical conductors 410 which transfer electrical charge or current from each sensor electrode to an associated connector pad 411 (see FIG. 5). Only the sensor electrodes and a thermistor 409 are located on the front side of the substrate. The predominant use of the back side of the substrate to route conductors allows the front side of the substrate (i.e., where space is at a much greater premium) to be reserved for those elements which must reside on the front side (such as the sensor electrodes). It should be noted that the conductors 410 and pads 411 are shown using broken lines in FIG. 5 to illustrate that an encapsulant 415 is applied over the conductors 410 and a portion of the pads 411. As will be discussed in greater detail below, solder is deposited over the pads 411 to provide an appropriate electrical and physical interface to a surface mount connector (not shown in FIG. 5). As will also be described in more detail below, the thermistor 409 (see FIG. 4) is also encapsulated after being deposited on the front of the substrate 405. While the term "deposited" is used throughout this document, the meaning is intended to be inclusive of all means for forming a structure in a layered device, including screening, plating, thick film techniques, thin film techniques, pressurized laminating, photolithographic etching, etc.

In accordance with one embodiment of the present invention, all of the connections which couple the sensors 403 to external devices are deposited on the back side of the substrate. These connections are spaced apart to provide the greatest possible insulation resistance. In one embodiment of the present invention, electrical conductors are deposited on a plurality of different fabrication layers deposited on the back side of the substrate 405. No sample or reference solution contacts the back side of the substrate, as will be clear from the description provided below. A conventional surface mount electrical connector is preferably mounted on the connector pads to provide an electrical conduction path through a mechanical interface from the sensors 403 to external devices which detect and process the electrical signals generated by the sensors 403.

The substrate 405 of the preferred embodiment of the present invention is essentially impervious to aqueous electrolytes and blood over relatively long periods of time (i.e., more than six months in the case of one embodiment of the present invention). In accordance with the preferred embodiment of the present invention, the inorganic substrate 405 is a sheet of approximately 0.025 inch thick commercial grade 96% alumina ($Al_2O_3$). The substrate 405 is preferably stabilized by a heat treatment prior to purchase. One such substrate is part number 4S200 available from Coors Ceramic Company, Grand Junction, Colo. Alternatively, the substrate may be any non-conductive essentially flat surface upon which the sensors may be deposited, as will be described in further detail below. For example, the substrate may be any silicon, glass, ceramic, wood product, non-conducting polymer or commercially available frit that can be used as a substantially smooth flat surface. However, the substrate preferably should be capable of withstanding the presence of an electrolyte having a pH of more than 6 to 9 and remaining essentially unaffected for an extended period of time (i.e., in the order of weeks).

Use of an alumina substrate provides the following advantages: (1) low thermal mass; (2) dimensional stability when subjected to aqueous electrolytes and blood for extended periods time; (3) establishes a mechanically and chemically stable substrate for use with thick film deposition techniques; (4) can be accurately laser drilled to high precision with very small diameter holes; (5) does not react with any of the materials which are used to fabricate sensors; and (6) very high electrical resistance. As a consequence of the fact that the assembly, including the inorganic substrate 405 and each deposited layer, is very stable and does not breakdown when subjected to aqueous electrolytes and blood, the sensor assembly 400 maintains very high isolation between (1) each of the sensors 403; (2) each of the sensors 403 and each electrical conductor; and (3) each of the electrical conductors.

Because the substrate 405 and each of the layers deposited thereon are stable and resists breakdown in the presence of aqueous electrolytes and blood, extremely high electrical resistance is maintained through the substrate. Accordingly, the present invention provides very high electrical isolation between each of the sensors 403, even after exposure to a corrosive environment over a relatively long period of time. This is advantageous for the following reasons. In accordance with one embodiment of the present invention, an isotonic reference medium (e.g., a gel or other a viscous solution having a known ion concentration) is placed over a reference electrode to provide a reference for potentiometric sensors which are fabricated on the substrate 405. The present sensor assembly 400 can be stored in a sealed pouch (not shown) having a humidity that reduces any evaporation of the isotonic reference medium. Storing the present invention in a sealed pouch having a controlled humidity also ensures that the sensors 403 remain partially hydrated during storage. Since the sensors 403 remain partially hydrated during storage of the sensor assembly 400, the sensors 403 of the present invention require minimal conditioning after installation. Therefore, having the sensors 403 stored in partially hydrated state greatly reduces the amount of time the user must wait before results can be attained from the sensors 403 of the present invention. This differs from prior art sensors which are stored in an essentially dry environment. Such prior art sensors must be assembled or preconditioned many hours prior to use. It is advantageous to provide a sensor assembly 400 which is available for use shortly after installation. For example, blood laboratories which use prior art blood analyzers must maintain at least two such prior art blood analyzers or risk being out of service for many hours after replacement of a sensor assembly (i.e., the time required to assemble, condition, calibrate, and rehydrate the sensors). The sensor assembly of the present invention can output results in as little as 10 minutes from the time the sensor assembly is installed, thus reducing the need for a second blood analyzer which would otherwise be required as a backup.

In accordance with the sensor assembly 400 shown in FIG. 4 and 5 the following sensors are provided: (1) sodium sensor 403h; (2) potassium sensor 403g; (3) calcium sensor 403f; (4) pH sensor 403e; (5) carbon dioxide sensor 403a; (6) oxygen sensor 403b; and (7) hematocrit value sensor 403c, 403d. A reference electrode 407 is also provided. The reference electrode is common to each of the potentiometric sensors (i.e., the sodium sensor 403h, potassium sensor 403g, calcium sensor 403f and carbon dioxide sensor 403a sensors) and provides a voltage reference with respect to each such sensor. It will be understood by those skilled in the art that these sensors, or any subset of these sensors, may be provided in combination with other types of sensors.

Fabrication of the Sensor Assembly of the Present Invention

The following is the procedure by which one embodiment of the present invention is fabricated. It will be understood by those of ordinary skill in the art, that there are many alternative methods for fabricating the present invention. Accordingly, the description of the preferred method is merely provided as an exemplar of the present invention.

Initially, a series of through holes are drilled through the substrate 405. Preferably, each through hole is laser drilled using a $CO_2$ laser to a diameter in the range of approximately 0.002–0.006 inches as measured on the front side of the substrate 405. By maintaining the small diameter of each through hole, the planar characteristic of an electrode which is deposited over the through hole is not distorted by the presence of the through holes. In the preferred embodiment of the present invention, thirteen holes are required, such that one hole is provided for each sensor, except for the hematocrit sensor 403c, 403d and the oxygen sensor 403b, each of which require two holes. The hematocrit sensor requires two holes in light of the two electrodes 403c, 403d. The oxygen sensor 403b preferably has one through hole for connection to the cathode of the sensor and one through hole for connection to the anode of the sensor. In addition, two through holes are preferably used for the connections to the thermistor 409. Also, two through holes are preferably used for the reference electrode 407 to reduce the risk of a defective through hole creating an open circuit. In the preferred embodiment of the present invention, each through hole that is associated with a sensor electrode is located under the location at which the associated sensor electrode to be deposited. Each such through hole is preferably located essentially at the center of the sensor electrode with the exception of the oxygen sensor 403b. However, in an alternative embodiment of the present invention, each through hole may be located anywhere underneath an electrode.

When the substrate 405 is a ceramic material, such as alumina, the substrate is preferably annealed after drilling all of the through holes at a temperature in the range of approximately 1000–1400° C., and more preferably in the range of approximately 1100–1200° C. Annealing the substrate after drilling ensures re-oxidation of a nonstoichiometric residue that attaches to the holes after the laser drilling. Without annealing, the residue (which is very reactive) contaminates the sensor electrodes, resulting in less pure electrode surfaces, which can lead to poor sensor performance. In the preferred embodiment of the present invention, the substrate is scribed after annealing. However, in an alternative embodiment of the present invention, the substrate may be scribed either before annealing, or not at all. Scribing the substrate allows several individual sensor assemblies formed in the same deposition processes on one substrate to be separated after all of the assemblies have been completed.

Once the through holes have been drilled and annealed, a thermistor paste is deposited in a predetermined pattern on the front side of the substrate 405 to form a thermistor 409 as shown in FIG. 4. In an alternative embodiment of the present invention, the particular geometry of the thermistor may vary from that shown in FIG. 4. In an alternative embodiment, the thermistor 409 is a discrete component which is not formed directly on the substrate. In the preferred embodiment of the present invention, the thermistor paste is part number ESL 2414, available from Electro-Science Laboratories, Inc. The thermistor paste 501 is preferably deposited to a thickness of approximately 15–29 $\mu$M when dried (10–22 $\mu$M when fired). The thermistor paste is oven dried and fired at a temperature of approximately 800–1000° C. for approximately 1–20 minutes. It will be understood by those skilled in the art that the thermistor 409 may be fabricated with any material that will provide information to an external control device by which the temperature of the sensor assembly 400 can be controlled. The thermistor is preferably be placed adjacent to any sensor that is particularly temperature sensitive or appropriately when measuring a temperature sensitive analyte. In an alternative embodiment of the present invention, a number of sensors and independently controllable heaters may be used to regulate the temperature of each sensor and the local temperature of the analyte at different locations along the flow path.

Once the thermistor paste has been deposited, dried, and fired, the substrate 405 is preferably placed in a vacuum fixture. The vacuum fixture (not shown) has a plurality of vacuum ports, each placed in contact with the opening of a through hole on the front side of the substrate. Preferably, each vacuum port is concurrently aligned with one of the through holes to create a relative low pressure within each through hole of the substrate with respect to the ambient pressure outside the through holes. A metallic paste, which is preferably compatible with the metal to be used to form the metallic layer of the electrodes of the electrolyte sensors 403h, 403g, 403f, as will be described in more detail below, is deposited over the through holes on the back side of the substrate 405. The deposited metal forms a conductive pad over the through hole. However, due to the vacuum applied to the front side of the substrate 405, a portion of the metal is drawn through the through holes. In accordance with the present invention, the metallic paste is preferably a silver paste, such as part number ESL 9912F, available from Electro-Science Laboratories, Inc. In accordance with the preferred embodiment of the present invention, the metallic paste is applied through a screen having a mesh density of 250 wires per inch (each wire having a diameter of approximately 0.0016 inches and a spacing of 0.0025 inches) and an emulsion thickness of approximately 0.0007 inches. The emulsion is developed to form a mask which allows the metal paste to pass through the screen only at the locations of the through holes on the back side of the substrate 405. The metallic paste is formed by the screen into columns above each through hole. Those columns of metal paste are then drawn down into the through holes by the reduction in pressure caused by the vacuum fixture. This procedure is preferably performed twice to ensure that each through hole is filled with the silver paste.

The substrate is then rotated to place the back side of the substrate 405 in contact with vacuum ports. The ports are aligned with the through holes over which the hematocrit electrodes 403c, 403d are to be deposited. The metal with which the front side of the through holes are filled is preferably selected to be compatible with the particular metal from which the electrode to be formed over the through hole is to be formed. In the preferred embodiment of the present invention, the hematocrit electrodes are formed using platinum. Therefore, the metallic material which fills the front side of these through holes and forms conductive pads on the front side of the substrate is preferably a silver/platinum paste, such as a mixture of silver paste, part number QS175, available from DuPont Electronics, and platinum paste, part number ESL 5545, available from Electro-Science Laboratories, Inc. The use of a silver/platinum paste presents a compatible interface between the platinum hematocrit sensor electrodes and the silver conductive material which fills the back side of the through holes which will underlie the hematocrit sensor electrodes. The mixture preferably has 50 parts silver, and 50 parts platinum. However, in an alternative embodiment, other alloys of silver and platinum may be used. Furthermore, any alloy which is compatible with platinum (i.e., with which platinum forms a solid solution), may be used. In a next screening process, each of the other eleven through holes (i.e., each of the through holes except the two over which the hematocrit electrodes 403b, 403c are to be deposited) are preferably filled from the front side of the substrate 405 using the same metallic paste that was previously used to fill the through holes from the back side of the substrate. Conductive pads, similar to the conductive pads formed on the back side of the substrate 405, are formed on the front side of the substrate 405. Filling the through holes from both the front and the back side of the substrate ensures that the entire through hole will be filled, and that a low resistance electrical contact will be made between the front and back side of the substrate through each through hole.

Figure 6A:
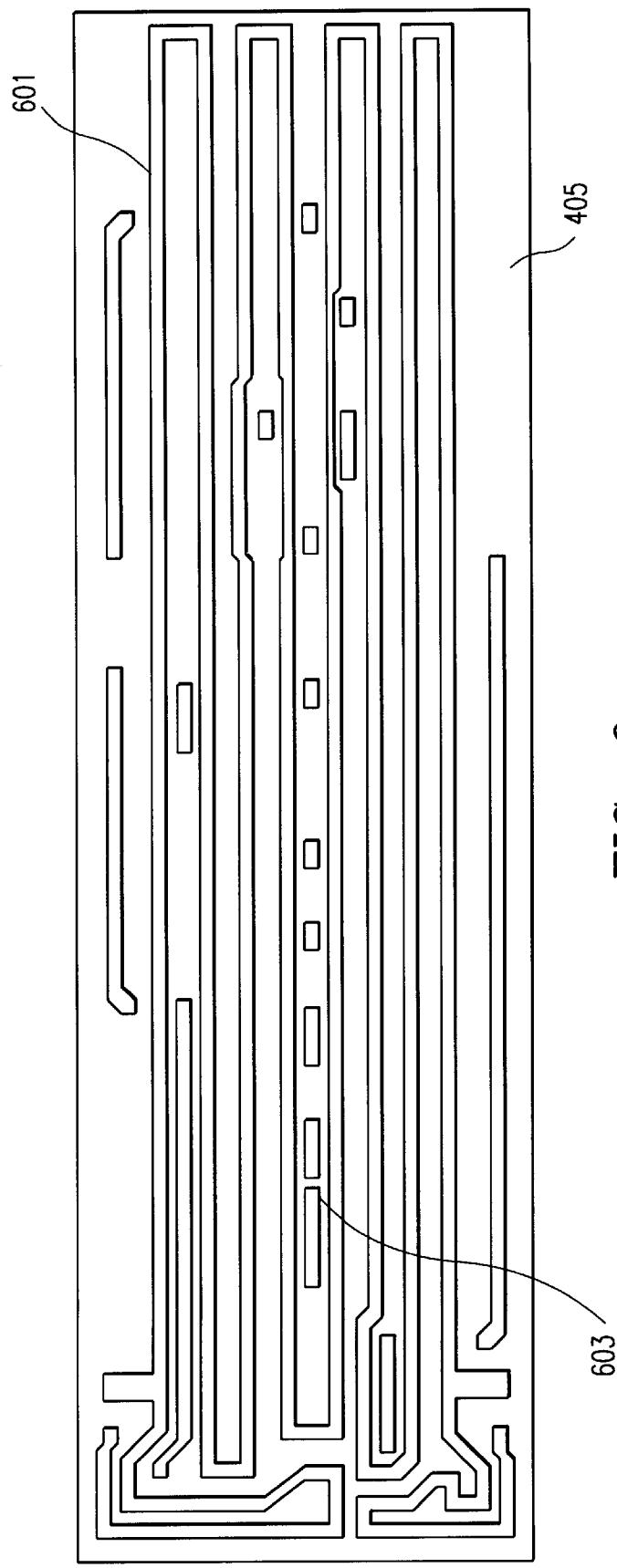
FIG. 6a is an illustration of one pattern to which a heater conforms when deposited on a substrate in accordance with the present invention.

FIG. 6a is an illustration of one pattern to which a heater 601 conforms when deposited on the substrate 405 in accordance with the present invention. In the embodiment shown, the heater 601 conforms generally to a complex serpentine pattern. FIG. 6a also shows a number of electrically conductive traces 603 which provide electrical conduction paths for current and/or electrical potential to be communicated from the electrodes of the sensors 403 to the pins of a connector to be affixed to the substrate, as will be described in greater detail below. The heater 601 is preferably deposited on the back side of the substrate 405. In accordance with one embodiment of the present invention, a heater paste blend including 10 parts of part number 9635-B, available from Heraeus Cermalloy, and 90 parts of part number 7484 available from DuPont Electronics is deposited to a thickness of 15–33 $\mu M$ dried (7–20 $\mu M$ fired). In accordance with one embodiment, a through hole vacuum may be applied to seal any through holes that remain open. It will be appreciated by those skilled in the art that the heater may be any heater device that provides a source of heat which can be readily controlled by a control device that receives information regarding temperature from the thermistor 409. It will also be appreciated that the particular routes taken by the conductors 603 may vary in alternative embodiments of the invention.

Figure 6B:
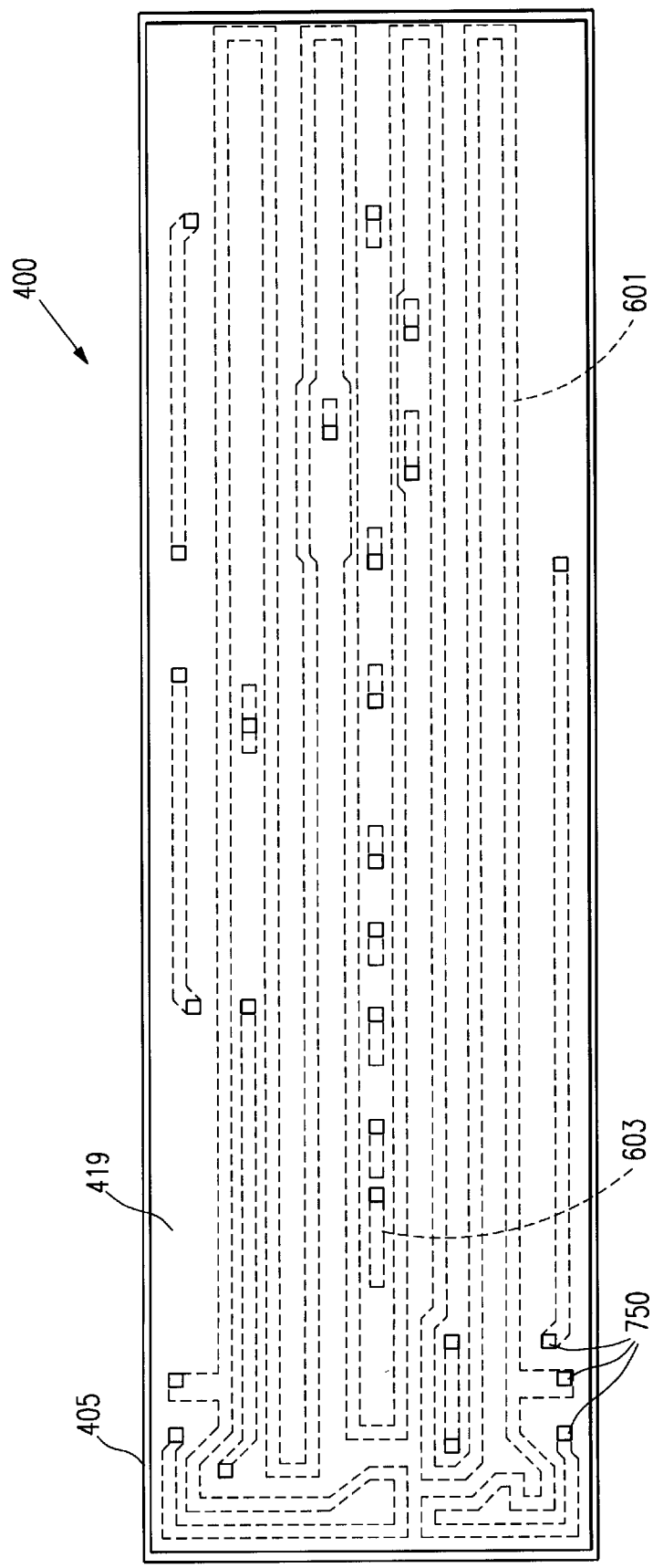
FIG. 6b is an illustration of the back side of a substrate after each of the dielectric layers have been deposited in accordance with one embodiment of the present invention.

Once the heater 601 and conductors 603 have been deposited, a series of dielectric layers 419 are deposited on the back side of the substrate 405 which electrically insulate the heater 601 and the conductors 603 from additional layers which are to be later deposited over the heater 601 and the conductors 603. The dielectric includes openings through which "vias" can be formed to provide electrical contact paths to the conductors 603 through the dielectric layers. A dielectric paste (such as part number 5704, available from E.I DuPont) is applied to the back side of the substrate 405, preferably using a conventional thick film screening technique. The screen used to apply the dielectric paste masks all locations except those at which a via is to be formed. FIG. 6b is an illustration of the back side of the substrate 405 after each of the dielectric layers 419 have been deposited. It should be noted that the heater 601 and conductors 603 are shown in broken lines to indicate the presence of the dielectric layer 419 over the heater 601 and conductors 603.

After two layers of the dielectric paste have been deposited, dried, and fired at a temperature of approximately 800°–950° C., a metallic paste, such as a palladium/silver composite, which in the preferred embodiment is part number 7484, available from E.I. DuPont, is deposited over those locations 750 at which vias are to be formed. In an alternative embodiment of the present invention, other noble metal mixtures can be used to achieve the desired resistance value within the available surface area. The metallic paste is then fired at 800°–950° C. for approximately 1 to 20 minutes. Two more layers of dielectric paste and metallic paste are deposited, each such layer being fired at 800°–950° C. for approximately 1 to 20 minutes directly after being deposited. It will be clear to those skilled in the art that other methods for depositing the dielectric layer and the vias may not require multiple layers of dielectric and metal. However, due to limitations on the thickness of layers which are deposited through a screen, more than one layer of both dielectric paste and metallic paste are preferably deposited. The dielectric layers between the conductive lines of the heater 601 build to a height which is nearly equal to the height of the dielectric layer over the heater 601, thus providing a relatively smooth surface at the back side of the sensor assembly 400.

Figure 7:
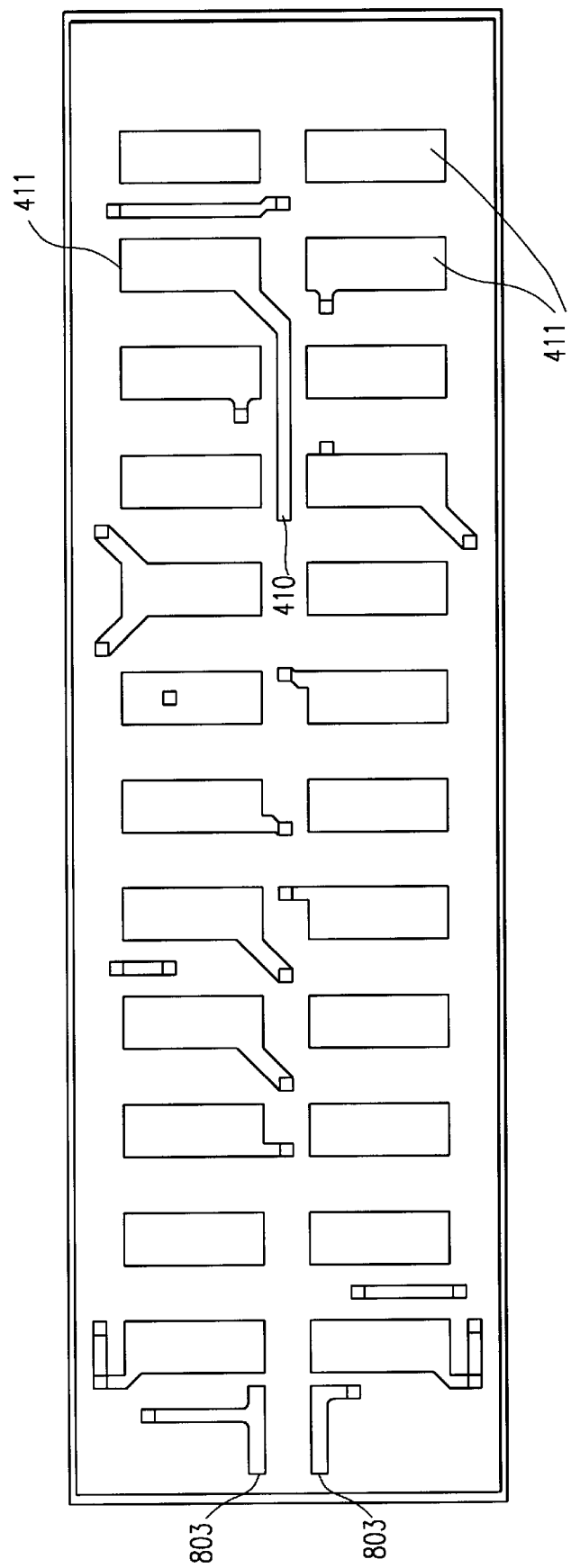
FIG. 7 is an illustration of the art work used to generate a screen, which in turn is used in the preferred embodiment of the present invention to deposit the second layer of conductors and connector pads.

After the last dielectric layer 419 is deposited, a second layer of conductors is deposited. FIG. 7 is an illustration of a second conductive layer, including the second layer of conductors 410, a plurality of connector pads 411, and connections 803 to the resistor 412 (see FIG. 5). In one embodiment of the present invention, the second conductive layer is formed from a metallic paste, such as palladium/silver, which in the preferred embodiment of the present invention is part number 7484 available from E.I DuPont. The second conductive layer is then oven dried and fired at a temperature in the range of approximately 800°–950° C. for approximately 1 to 20 minutes. The conductors 410 and conductive connector pads 411 complete the connection between the sensor electrodes and external devices (not shown) coupled to the connector fixed to the connector pads 411. The second layer of conductors is oven dried and fired at a temperature in the range of approximately 800°–950° C. for approximately 1 to 20 minutes.

In accordance with the present invention, conductors 603, 410 are deposited on only two layers (i.e., the heater layer and the connector pad layer). However, in an alternative embodiment of the present invention in which the geometry of the sensor assembly 400 makes it difficult to route the conductors from each sensor to an appropriate electrical contact pad to which a connector is to be electrically coupled, more than two layers having conductors may be used. In such an embodiment, each such conductor layer is preferably separated by at least one layer of insulating dielectric material.

Figure 8:
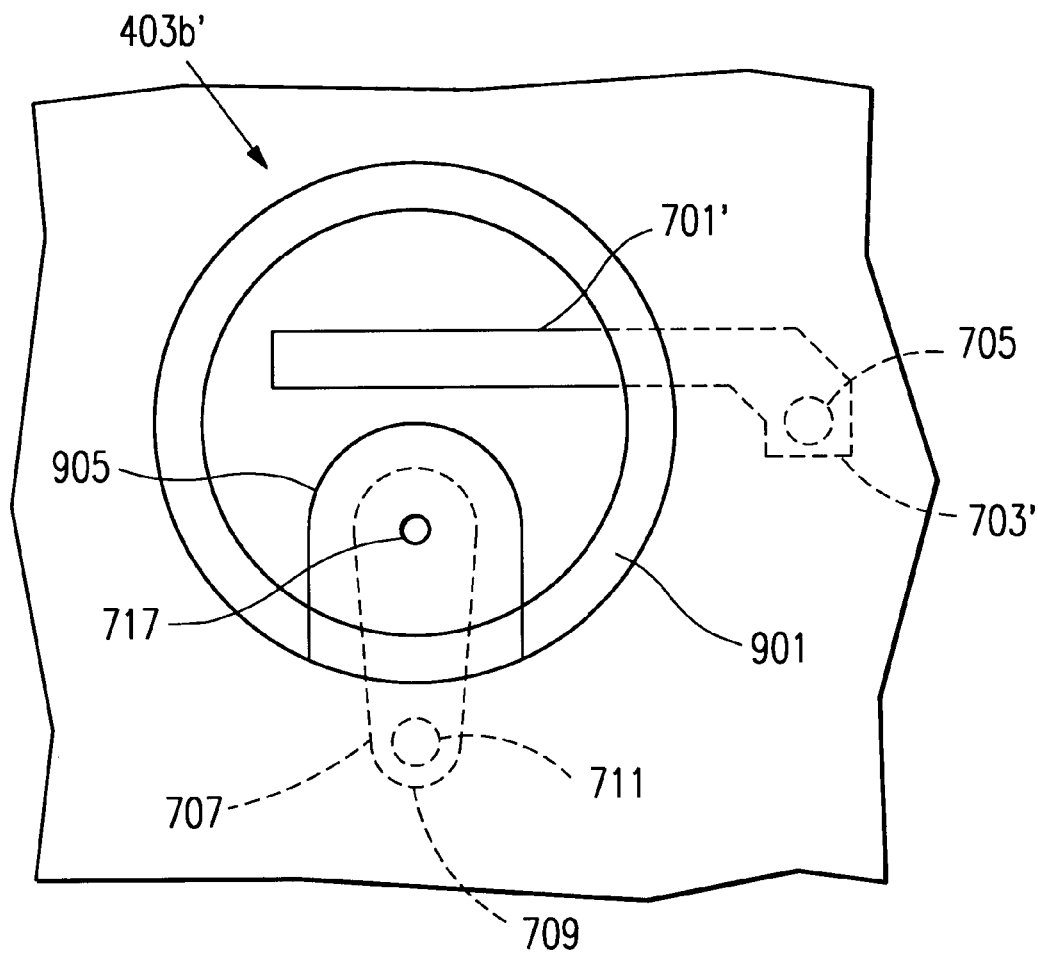
FIG. 8 is an illustration of an oxygen sensor in accordance with the preferred embodiment of the present invention.

After the second layer of conductors has been deposited on the back side of the substrate 405, each of the layers which form the electrodes of the sensors 403 are deposited on the front side of the substrate 405. Concurrent with the deposition of the first metal layer of each electrode, contacts 414 to the thermistor 409 are deposited to couple the thermistor to the through holes that are adjacent the thermistor 409 (see FIG. 4). FIG. 8 is an illustration of an oxygen sensor 403b' in accordance with an alternative embodiment of the present invention. Both the oxygen sensor 403b and 403b' are essentially conventional amperometric cells. The only difference between the oxygen sensor 403b shown in FIG. 4 and the oxygen sensor 403b' shown in FIG. 8 is the shape of the anodes 701, 701'. In accordance with the preferred embodiment of the present invention, the anodes 701, 701' are essentially straight conductors which deflect from straight at the distal end 703, 703'. Preferably, the area of the anode is a minimum of 50 times greater than the area of the cathode to ensure the most stable operation. In addition, the distance between the anode and the cathode is preferably approximately 0.020–0.030 inches to ensure that the potential developed across the anode to cathode is not too great. It should be noted that the anode of the oxygen sensor may be configured to conform to any number of alternative shapes. These two shapes are provided merely as exemplars of the shape of the anode in accordance with two particular embodiments of the present invention. In one embodiment of the present invention, a metal, such as silver paste, part number QS 175, available from DuPont Electronics, is deposited to form the anode 701, 701' of the oxygen sensor 403b'. Alternatively, any metal suitable for use in forming the anode of an amperometric cell may be used, such as platinum, ruthenium, palladium, rhodium, iridium, gold, or silver. A distal end 703, 703' of the anode 701, 701' is deposited over one of the above described through holes 705 through the substrate 403.

The cathode conductor 707 is then deposited. A distal end 709 of the cathode conductor 707 is deposited over another of the through holes 711 through the substrate 403. The cathode conductor 707 and the anode 701, 701' are oven dried and fired at a temperature of approximately 800° C. to 950° C. for approximately 1 to 20 minutes.

Figure 9:
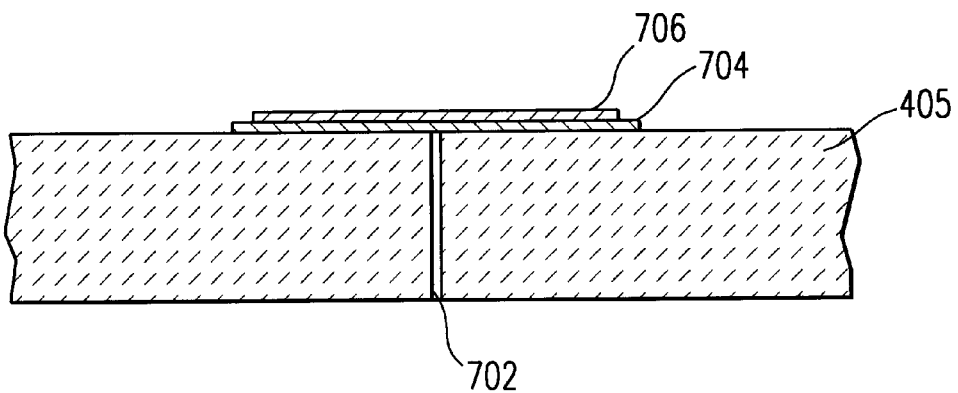
FIG. 9 is a cross-sectional view of a portion of a substrate through which a sensor through hole is formed and on which metal layers of an electrolyte sensor electrode have been deposited in accordance with one embodiment of the present invention.

FIG. 9 is a cross-sectional view of a portion of the substrate 405 through which a sensor through hole 702 is formed and on which metal layers of an ion sensitive sensor electrode have been deposited. Concurrent with the deposition of the oxygen sensor 403b, and by deposition of the same type of material (preferably silver) deposited to form the metallic layer of the anode 701, 701' of the oxygen sensor 403b, a first metallic layer 704 of each of the electrodes associated with each of the other sensors 403a, 403e–403h and the reference electrode 407 are deposited on the substrate over a through hole 702. In the case of sensors 403a, 403e–403h which are to have a polymeric membrane disposed over the metallic layer, a second metallic layer 706, preferably of the same material as the first metallic layer 704, is deposited over the first metallic layer 704 in order to reduce any distortion in the flatness of the surface due to the presence of the through hole 702 located beneath the first metallic layer 704. That is, electrodes formed over a through hole 702 with only one layer of metallic material tend to develop a depression over the through hole 702. Such a depression is generally of no consequence if the electrode is not to be coated with a polymeric membrane.

However, in sensors which have polymeric membranes, such a depression can cause the membrane to become embedded in the electrode 704. As a result of this distortion, optimal performance would not be achieved. That is, very uniform membrane geometry is important to achieving optimal sensor function and performance. This can be understood in light of the fact that in the preferred embodiment of the present invention, the thickness of a polymeric membrane that is applied over the metallic layers 704, 706 is determined by pouring a controlled volumetric quantity of a membrane solution into a sensor cavity having well defined dimensions (as will be discussed further below). The membrane formed over the metallic layer 706 is very thin (i.e., approximately 5–250 $\mu$M). Any variation in the thickness of the membrane at one point, effects the thickness of the membrane at each other point. Such variations in the thickness of the membrane adversely effect the performance of the sensor 403. Therefore, if a depression exists in the metallic layer which underlies the polymeric membrane, the membrane will be thicker over the depression, and thus thinner over the remainder of the electrode. Depositing a second metallic layer 706 smooths any such depression which might otherwise exist. The second metallic layer 706 preferably has a different diameter than the first layer 704 in order to reduce the chances that the metallic layers will puncture the polymeric membrane due to the abrupt edge that would be formed at the perimeter if both the first and second metallic layers 704, 706 were to have the same diameter. Since the presence of a depression is insignificant in electrodes of sensors which do not require a thin membrane, these sensors are preferably formed having only one metallic layer 704.

The preferred dimensions for the metallic layers 704, 706 of each sensor in accordance with one embodiment of the present invention are provided below. It will be understood by those skilled in the art that other dimensions may be quite suitable for fabricating sensors. However, the dimensions presented reflect a tradeoff between reduced impedance and reduced size. A tradeoff is required because of the desire to form the sensor in as small an area as possible, and the competing desire to form a sensor which has a relatively low impedance. These two goals are incompatible because of the inverse relationship between size and impedance. That is, in general, size is inversely proportional to impedance. Therefore, the greater the size of the sensor electrode, the smaller the impedance of that electrode.

The diameter of the first metallic layer 704 of the $CO_2$ sensor 403a, the pH sensor 403e, and each of the electrolyte sensors 403f, 403g, 403h is 0.054 inches. The diameter of the second electrode layer 706 of each of these sensors is 0.046 inches. The second layer 706 is deposited over the first layer 704. The metallic layer 704 of the reference electrode is generally rectangular, having rounded corners with radius equal to one half the width of the electrode. The width of the electrode is preferably 0.01 inches, and the length is preferably 0.08 inches. It will be understood by those skilled in the art that the reference electrode 407 may be formed in numerous other shapes. After the first metallic layer 704 is deposited, the substrate 405 is oven dried and fired at approximately 800°–950° C. for approximately 1–20 minutes. After deposition, the second metallic layer 706 is similarly dried and fired. Each of the metallic layers 704, 706 is preferably 16–36 $\mu$M thick after drying, and 7–25 $\mu$M thick after firing.

Figure 10:
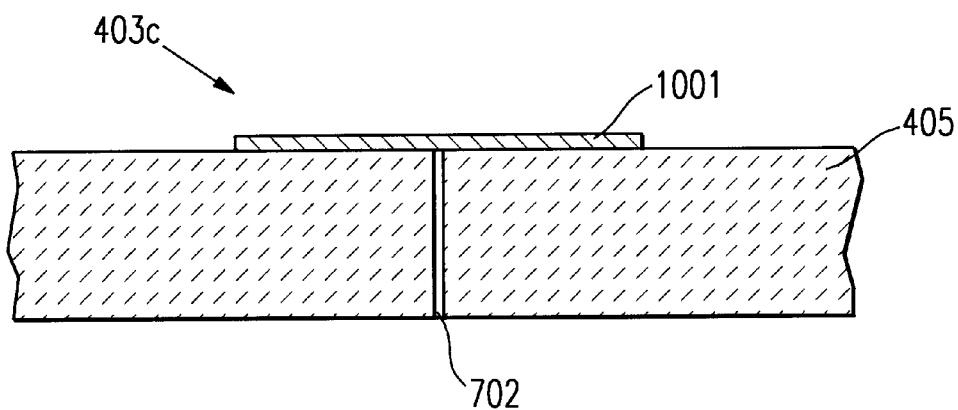
FIG. 10 is a cross-sectional view of one of the hematocrit sensor electrodes in accordance with one embodiment of the present invention.

FIG. 10 is a cross-sectional view of one of the hematocrit sensor electrodes 403c. Only one of the two electrodes 403c, 403d are shown, since each are essentially identical. In accordance with the preferred embodiment of the present invention, the metal used to form the electrodes of the hematocrit sensor 403c, 403d differs from the metal 704, 706 used to form the electrodes of the electrolyte sensors 403f, 403g, 403h, the pH sensor 403e, the oxygen sensor 403a, and the reference electrode 407. Therefore, in the preferred embodiment, the electrodes of the hematocrit sensor 403c, 403d are formed by depositing a third metallic layer 1001. Since no polymeric membrane is to be placed over the metallic layer 1001 of the hematocrit electrodes 403c, 403d, the hematocrit electrodes 403c, 403d preferably only have one metallic layer. In the preferred embodiment of the present invention, the metal used to form the electrodes for the hematocrit sensor 403c, 403d is a cermet platinum conductor, such as part number ESL 5545, available from Electro-Science Laboratories, Inc. The diameter of the metallic layer 1001 of each hematocrit sensor electrode is 0.054 inches. The hematocrit sensor electrodes 403*c*, 403*d* are preferably spaced approximately 0.15 inches apart.

After forming the metallic layer 1001 of the hematocrit sensor electrodes 403*c*, 403*d*, the cathode conductor 707 (see FIG. 8) is deposited. In accordance with the preferred embodiment of the present invention, the cathode conductor 707 is formed from a gold paste, such as part number ESL 8880H, available from Electro-Science Laboratories, Inc. It will be understood by those skilled in the art that the cathode conductor 707 may be fabricated from any metal commonly used to form a cathode of a conventional amperometric cell, However, it should be noted that the level of contaminants in the paste will effect the sensor characteristics. Furthermore, in an alternative embodiment of the present invention the particular geometry of the cathode conductor 707 may vary from that shown in FIG. 8. At the same time that the cathode conductor 707 is deposited, a pair of laser targets 417, 418 are preferably deposited. The laser targets 417, 418 provide a reference which is used to form a cathode 717, as will be discussed in greater detail below. Once deposited, the cathode conductor 707 is dried and fired at a temperature of 800°–950° C. for approximately 1 to 20 minutes.

Figure 11:
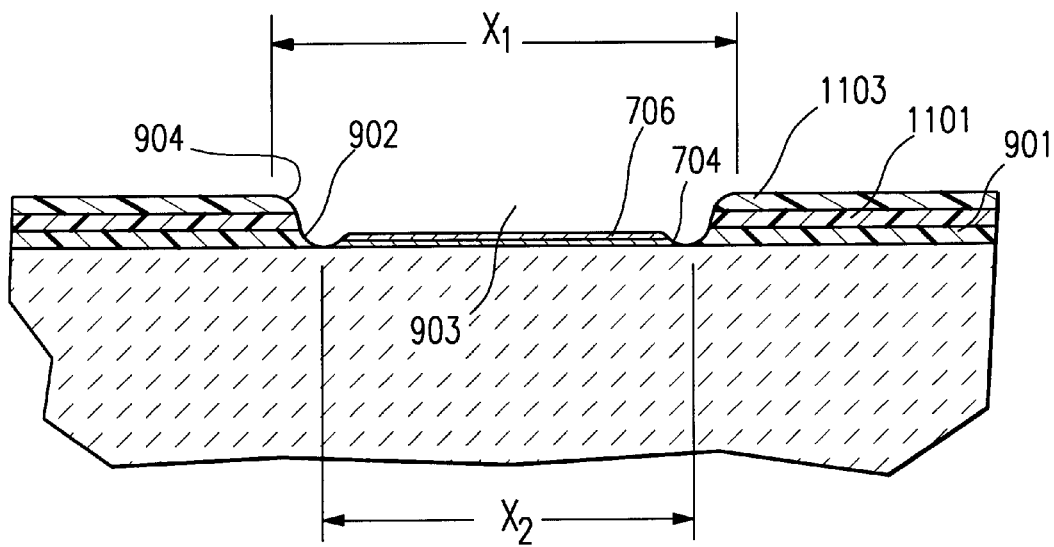
FIG. 11 is a cross-sectional view of a sensor showing the first layer of encapsulant in accordance with one embodiment of the present invention.
Figure 12:
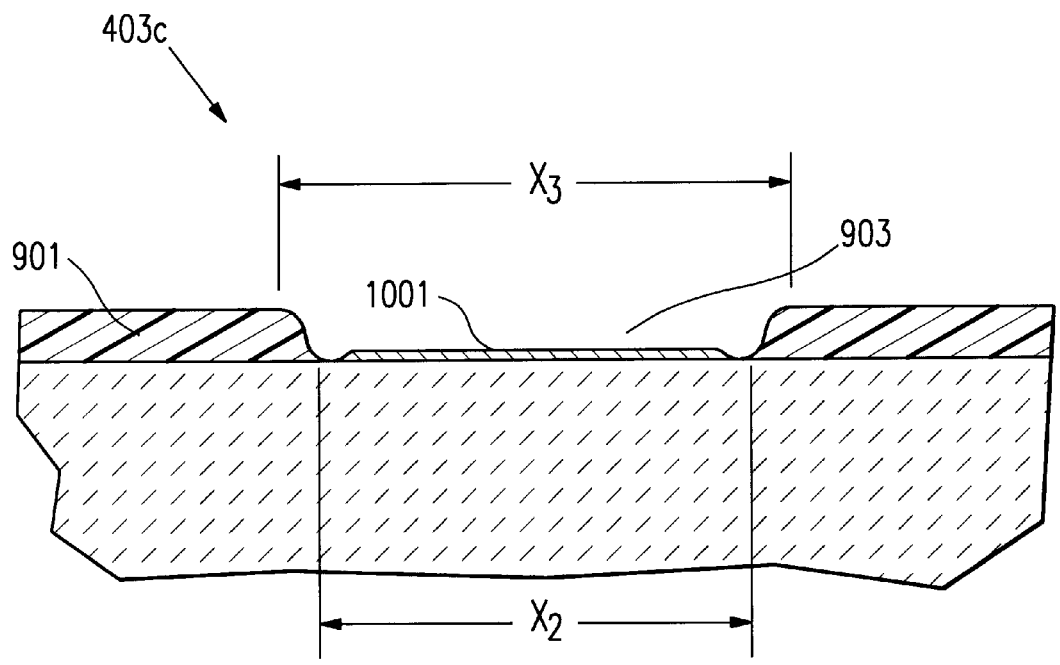
FIG. 12 is a cross-sectional view of one of the hematocrit sensors showing the first layer of encapsulant in accordance with one embodiment of the present invention.

Once the cathode conductor 707 has been dried and fired, a resistor 412 is preferably deposited on the back side of the substrate 405, as shown in FIG. 5. The resistor 412 is coupled in series with the heater 601 in order restrict the current to an appropriate level through the heater during electrical conduction. Next, a first layer of an encapsulant is deposited on the front side of the substrate 405. FIG. 11 is a cross-sectional view of a sensor 403 showing the first layer of encapsulant 901. FIG. 12 is a cross-sectional view of one of the hematocrit sensors 403*c* showing the first layer of encapsulant 901. It should be noted that FIGS. 10 and 11 are not to scale and that the first layer of encapsulant 901 is preferably very thin (i.e., preferably only a few microns). The encapsulant 901 is deposited essentially over the entire front side of the substrate 405 in order to prepare the surface of the substrate to receive a polymer, as will be discussed in more detail below. In accordance with the preferred embodiment of the present invention, the encapsulant 901 is deposited through a screen using a conventional thick film technique. The screen preferably has a density of 250 wires per inch (with a wire diameter of approximately 0.0016), and an emulsion thickness of 0.0007 inches. The screen masks the encapsulant 901 from forming over the thermistor 409 and metallic layers 704, 706 of each of the sensors. However, in the preferred embodiment, the distal end 703, 703' of the anode 701, 701' and the entire cathode conductor 707 are encapsulated, as shown for example in FIG. 8. A high quality encapsulant is preferably used which will not undergo chemical alteration in the presence of a caustic solution (such as blood or other aqueous solvents). For example, in the preferred embodiment, the encapsulant is part number ESL 4904, available from Electro-Science Laboratories, Inc. However, the thermistor 409 is preferably not encapsulated with the higher quality encapsulant, since such high quality encapsulants typically require firing at high temperatures (850° C., for example in the case of encapsulant used in the preferred embodiment). Such high temperatures will cause the thermistor 409 to deform. Therefore, only after firing the high quality encapsulant can the thermistor be encapsulated. Accordingly, in the preferred embodiment of the present invention, the thermistor 409 is encapsulated with an encapsulant which may be fired at a low temperature.

In the preferred embodiment of the present invention, a second layer of encapsulant 905 is deposited only over the cathode conductor 707 in order to ensure that the cathode conductor is securely isolated. In one embodiment of the present invention, the second layer of encapsulant 905 is applied in two screening procedures in order to provide a total desired thickness for both the first and second layers of encapsulant of approximately 27–47 $\mu$M. While alternative embodiments of the present invention may employ an encapsulant layer which differs in thickness, a thickness in the range of approximately 27–47 $\mu$M provides satisfactory isolation of the cathode conductor 707. Furthermore, i single layer of encapsulant provides sufficient treatment of the surface of the substrate 405 to allow a polymer to be deposited and bonded to the substrate 405, as further explained below.

After the encapsulant 901, 905 are deposited over the cathode conductor 707, a hole is preferably laser drilled through the encapsulant 901, 905 to expose a portion of the cathode conductor 707, and thus form the cathode 717. The cathode may be laser drilled either before or after firing the encapsulant. The laser targets 417, 418 are used to visually align the laser apparatus in order to drill the hole at the correct location. That is, the lower horizontal edge of the target 417 identifies a line in the horizontal direction. Likewise, the leftmost edge of the laser target 418 identifies a line in the vertical dimension. The cathode is then formed at the intersection of these two lines. Alternatively, the cathode 717 is formed by masking a portion of the cathode conductor 707 in order to prevent the encapsulant 901 from forming over that portion of the cathode conductor 707. In yet another embodiment of the present invention, the cathode 717 may be exposed by a chemical etch. It will be clear to those skilled in the art that numerous other methods may be used to expose a portion of the cathode conductor 707 in order to form a cathode 717.

After applying the first and second encapsulant layers to the front of the substrate 405, a thermistor encapsulant 413 is deposited over the thermistor 409. The thermistor encapsulant 413 can be fired at a relatively lower temperature (such as approximately 595° C.) and thus firing of the thermistor encapsulant 913 does not disturb the geometry of the thermistor 409. In one embodiment of the present invention, the thermistor encapsulant 413 is applied in two screenings in order to achieve a desired thickness and to ensure that no pores are formed in the encapsulant 413. It will be understood by those skilled in the art that the encapsulant over the thermistor 409 should remain relatively thin in order to avoid adding any delay in the sensing of the temperature of the sensor assembly 400. In addition, a resistor encapsulant 415 is deposited over the resistor 412 on the back side of the substrate 405. The resistor encapsulant 415 is preferably the same material as the thermistor encapsulant 413.

After the resistor encapsulant 413 has been deposited on the back side of the substrate 405, a first polymer layer 1101 is deposited on the front side of the substrate 405. The first polymer layer (together with the first encapsulation layer 901) forms the lower wall 902 of a plurality of sensor cavities 903 (see FIGS. 10 and 11). The polymer of the preferred embodiment of the present invention is screen printable, absorbs minimal moisture, chemically isolates the membrane chemistries of adjacent cavities, and produces a strong solution bond with the polymeric membrane also forms a strong bond with the dialectic layers when exposed at the inside surface of the cavity by an appropriate solvent (such as tetrahydrofuran, xylene, dibutyl ester, and carbitol acetate or any cyclohexanone solvent) in the membrane formation, as will be discussed in further detail below.

The polymer used to form the layer 1101 is preferably a composition of 28.1% acrylic resin, 36.4% carbitol acetate, 34.3% calcined kaolin, 0.2% fumed silica, and 1.0% silane, noted in percentage by weight. The acrylic resin is preferably a low molecular weight polyethylmethacrylate, such as part number 2041, available from DuPont Elvacite. The calcined kaolin is preferably a silaninized kaolin, such as part number HF900, available from Engelhard. The silane is preferably an epoxy silane, such as trimethoxysilane. Silane bonds to the hydroxyl groups on the glass encapsulant over the substrate, and yet is left with a free functional group to crosslink with the resin's functional group. In accordance with one embodiment of the present invention, the first polymer layer 1101 is deposited in three screening processes in order to attain the desired thickness (i.e., preferably approximately 0.0020 inches). The first polymer layer is dried after each screening process. A second polymer layer 1103 is deposited to form an upper wall 904 of the sensor cavities 903. The first and second polymer layer 1101, 1103 differ only in the diameter across the cavity at the lower cavity wall 902 and at the upper cavity wall 904 and the number of screening processes that are required to achieve the desired depth. In the case of the second polymer layer, 10 screening procedures are performed. The second polymer layer is dried after each screening procedure. In addition, after the last two procedures, the polymer is both screened and cured. In the preferred embodiment of the present invention, the last screening procedure may be omitted if the second polymer layer has achieved the desired thickness (i.e., preferably 0.0075–0.0105 inches after curing).

The diameter of the cavities are preferably carefully controlled to aid in controlling the deposition of the membranes which are placed over the electrodes of the sensors (i.e., the shape and thickness of the membranes). That is, the sensor cavities enable a droplet of polymeric membrane solution to be captured and formed into a centrosymmetric form over the electrode with sufficient surface contact with the walls of the cavity to assure that the membrane remains physically attached.

Preferably, the sensor cavities 903 for the pH sensor 403e, the electrolyte sensors 403f, 403g, 403h, and the hematocrit sensor 403c, 403d, each have a total depth of approximately y=0.0075 inches, a diameter at the upper wall 904 of approximately $x_1$=0.070 inches, and at the lower wall of approximately $x_2$=0.06 inches (see FIG. 11). The diameter $x_3$ of the carbon dioxide sensor cavity 903 is slightly larger than the diameter $x_1$ of the electrolyte sensors 403e–403f and the hematocrit sensor electrodes 403b, 403c. In the preferred embodiment, the diameter $X_3$ is equal to 0.078 inches (see FIG. 12). It should be understood that a membrane of the same thickness may be produced by increasing the diameter of the sensor cavity 903 and increasing the volumetric quantity of the membrane solution that is applied to the sensor in proportion to the increase in the volume of the cavity. Likewise, the same thickness can be maintained by decreasing the diameter of the sensor cavity 903 and proportionally decreasing the volumetric quantity of the membrane solution. It will be clear to those skilled in the art that in an alternative embodiment of the present invention, the sensor cavities may have a shape other than the generally cylindrical shape disclosed above. For example, in accordance with one embodiment of the present invention, the electrodes are formed in an oval shape to reduce the required volume of a sample. However, in the preferred embodiment, the sensor cavities are either cylindrical or generally conical.

Once the sensor cavities 903 have been formed and the polymer layers dried, each silver potentiometric electrode is chemically chlorodized to create a layer of silver chloride. The cavity 903 of each ion sensitive sensor is filled with an electrolyte which is appropriate to the particular type of sensor 403. In the preferred embodiment of the present invention, the electrolyte used in the sodium, potassium and calcium electrolyte sensors are ions of inorganic salts that disassociate in solution, such as NaCl, KCl, or $CaCl_2$. In accordance with one embodiment of the present invention, the electrolyte solution is evaporated to a solid form. Alternatively, the electrolyte remains a liquid or a gygroscopic water insoluble gel that acts as a support to immobilize the electrolyte. In accordance with one embodiment of the present invention, such a gel may crosslinked after transfer to the cavity 903. Furthermore, in accordance with one embodiment, the gel undergoes polymerization by a catalyst contained within the solution. In one such embodiment, the gel is polymerized by activating a catalyst with heat or radiation.

The gelled polymer is preferably one of the following, or a mixture of these: (1) starch, (2) polyvinyl, (3) alcohol, (4) polyacrylamide, (5) poly (hydroxy ethyl methacrylate), or (6) polyethylene glycol or polyethylene oxide ether, or another long chained hygroscopic polymer. Hygroscopic polysaccharides or natural gelatin are preferably added to the electrolyte solution.

The electrolyte used in the pH sensor preferably has an acidic pH in the range of about 3–7. In accordance with one embodiment, the electrolyte is an aqueous solution of potassium hydro phosphate ($KH_2PO_4$), preferably has 13.6 grams of potassium hydro phosphate in one liter of deionized water. The electrolyte suppresses the reaction of carbon dioxide and water to minimize the extent to which the carbon dioxide influences the pH of the electrolyte. This favors the pH response for pH measurement and minimizes the response of $CO_2$. The electrolyte for $pCO_2$ sensor is initially at an alkaline in the range of approximately 7–14. However, in the preferred embodiment of the present invention, the electrolyte is approximately 8 due to the presence of bicarbonate ions. In accordance with the present invention, the electrolyte for the $pCO_2$ sensor is preferably 0.02 moles of sodium bicarbonate in a liter of deionized water. Solutions in either liquid or gel phase may be used. A sensor which includes such an electrolyte is also described in U.S. Pat. No. 5,336,388, assigned to PPG Industries, Inc, which is incorporated in its entirety by this reference.

The electrolyte of the oxygen sensor 403a provides a low impedance contact across the anode and cathode and not to create a standard chemical potential as is the case in the aforementioned potentiometric sensors. Suitable electrolytes are NaCl and KCl. The electrolyte may be either a fluid or a gel. The preferred use of the electrolyte is in a buffered solution such as one having 0.1 mole potassium hypophosphite ($KH_2PO_3$).

All of the aforementioned electrolytes are preferably encapsulated by a selectively permeable, hydrophilic membrane that serves to trap the electrolyte against the electrode. Such membranes include a polymer, a plasticizer, an ionophore, a charge screening compound, and a solvent. The membranes are selective permeable barriers that restrict the free passage of all but the desired ion. The membrane preferably comprises an inert iypophilic polymer dispersed in an organic plasticizer.

Water molecules will rapidly diffuse across these membranes. In accordance with one embodiment of the present invention, the inert polymer is polyvinlychoride (PVC). However, in an alternative embodiment, other ion permeable polymers may be used, such as (1) copolymeric vinyl ethers, (2) porous polytetraflourethelene (PTFE), (3) silicones, (4) cellulose acetate, (5) poly (methlymethacrylate), (6) polystyrene acrylate, (7) methacrylate copolymers, (8) polyimides, (9) polyamides, (10) polyurethanes, (11) polybisphenol-A carbonate (polysiloxane/poly(bisphenol-A carbonate) blocked copolymer, (12) poly (vinylidenechloride); and (13) lower alkyl acrylate and methacrylate copolymers and polymers. It will be clear to those skilled in the art that this list is not exhaustive, and that other such ion permeable polymers may be used.

Furthermore, suitable plasticizers include (1) dioctyl adipate, (2) bis(2-ethylhexyl)adipate, (3) di-2-ethlylhexyladipate, (4) dioctyl phthalate, (5) 2-nitrophenyl octyl ether (NPOE), (6) diotcyl sebacate, (7) nitrobenzene, (8) tri(2-ethylhexyl) phosphate, (9) dibutyl sebacate, (10) diphenyl ether, (11) dinonyl phthatlate, (12) dipenyl phthalate, (13) di-2-nitrophenyl ether, (14) glycerol triacetate, (15) tributyl phosphate, (16) dioctyl phenyl phosphate, and similar long chained ethers and hydrocarbons, and combinations thereof. In the preferred embodiment, a combination of bis(2-ethylhexyl)adipate, 2-nitrophenyloctylether or 0-nitrophenyloctylether (NPOE), and nitrobenzene are used as the plasticizer for the pH and $CO_2$ sensor. Dioctyl Phthalate is preferably used as the plasticizer in the calcium, potassium and sodium sensors.

The membrane polymer and plasticizers are preferably soluble in organic solvents, such as cylohexanone, tetrahydofuran, xylene, dibutyl ester, and carbital acetate. In accordance with one embodiment of the present invention, such solvents are removed from the membrane after application over the electrode by vacuum drying at ambient temperatures or low temperatures less than 100° C. The solvent softens the organic layer on the substrate that supports the membrane and encapsulates the internal electrolyte over the electrode while allowing penetration of the membrane by the ion via the complexing agent or ionophore. In accordance with one embodiment of the present invention, after encapsulation, the internal electrolyte is hydrated for a predetermined period prior to use to allow water vapor to permeate the membrane and form an internal electrolyte solution producing a chemically and physically uniform distribution of charge on the electrode.

It will be understood by those skilled in the art that any ionophore or ion exchanger that mediates the interaction of the ion with environment and which facilitates the translocation of the ion would be suitable for use in the membrane of the present invention. For example, in the present invention the ionophore or ion exchanges may be another of the following: (1) tridodecylamine (TDDA), (2) tri-n-dodecylamine, (3) valinomycin ($K^+$); (4) methyl monesin ($Na^+$), or (5) tridodecylmethyl-ammonium chloride ($Cl^-$). A lipophilic organic anion serves as a balancing specie, such as tetraphenyl borate is preferably present to provide electroneutrality. The membranes of the present invention provide accurate detection and fast response over long periods of use.

The oxygen sensor membrane restricts access of electroactive materials other than oxygen to the electrode surface while allowing free diffusion of oxygen to the electrode surface.

All membrane solutions arc dispenses in the sensor cavities using automated fluid dispensing systems. These systems have three main parts: (1) a horizontal x-y-z motorized and programmable table (such as those available from Asymtek of Carlsbad, Calif.); (2) a precision fluid metering pump (such as those available from Fluid Metering, Inc. of Oyster Bay, N.Y.); and (3) a personal computer control unit.

All three parts are linked by a digital communication protocol. Software for set-up and dispensing a sequence of liquid microvolumes communicates the x, y, and z positions to the table, and timing of the dispensing pump controller. At each cavity, the metering pump transfers a preset volume of electrolyte or membrane solution through fine diameter tubing from a supply reservoir to a needle or nozzle mounted on the motorized axes of the table and then to the cavity. The fluid may be successfully dispensed with a number of different pumps; pinch tube, rotary positive displacement or diaphragm valves. The drop size is generally no larger than one diameter of the sensor cavity.

After dispensing the aqueous or organic solution, the membrane is formed by drying or curing liquid. Drying removes the solvent components by evaporation. The drying process may be performed by heating or applying a vacuum pressure. Some organic solutions may be cured either thermally or by exposure to ultra-violet radiation.

The combination of the geometry, membrane composition, and aqueous or organic internal electrolyte have been found to yield membranes of minimal thickness, with controlled diffusion paths so that potentiometric sensor to a varying concentration of gas. Elimination of in-plane electrical connections to the electrode by use of a subminiature through hole assures better control of the electrochemical process. In addition, the use of subminiature through holes improves the flatness of the bonding surface of the polymer coating laminated on the substrate for better bonding and sealing of the flow cell.

Figure 13:
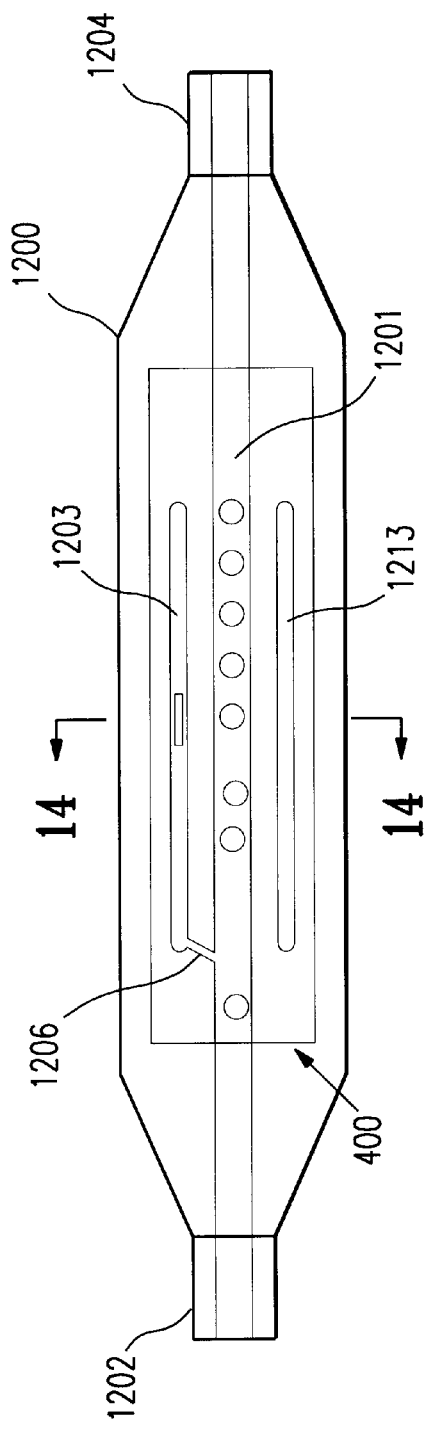
FIG. 13 is a top plan view of the sensor assembly installed within a plastic encasement.
Figure 14:
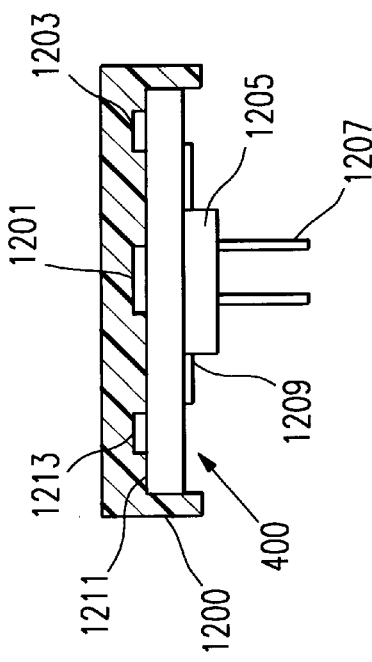
FIG. 14 is a cross-sectional view of the sensor assembly installed in the plastic encasement.

FIG. 13 is a top plan view of the sensor assembly 400 installed within a plastic encasement 1200. FIG. 14 is a cross-sectional view of the sensor assembly 400 installed in the plastic encasement 1200. After each of the sensors have been completed, the pads 411 are plated with solder. The solder provides an electrical and mechanical interface between the pads 411 and contacts 1209 of a conventional electrical surface mount connector 1205. The contacts 1209 of the surface mount connector 1205 are soldered to the pads 411 in a conventional manner. In addition, the connector 1205 is preferably secured to the substrate 405 by an adhesive, such as an epoxy glue. Electrically conductive pins 1207 of the conventional connector 1205 permit the sensor assembly 400 to be easily installed and in, and removed from, a blood analyzer (not shown). Use of a conventional surface mount connector 1205 result in a reliable interface to the blood analyzer instrumentation, provides a simple design, low cost construction, an simple test interface, and allows critical connections to be spaced apart to ensure high electrical resistance between each critical connection. Furthermore, the conventional surface mount connector 1205 allows the present invention to be mass produced at low cost, and makes the present invention analogous to familiar semiconductor dual-in-line packages.

The front side of the sensor assembly 400 is enclosed in the plastic encasement 1200 which forms a flow cell 1201 and a reference cell 1203. A lap joint 1211 is preferably formed between the sensor assembly 400 and the encasement 1200. In accordance with the preferred embodiment of the present invention, an adhesive, such as epoxy glue, is used to secure the sensor assembly 400 in the encasement 1200. The encasement 1200 is formed with inlet and output ports 1202, 1204, respectively. The inlet and outlet ports 1202, 1204 allow a sample to be injected into, and discharged from, the flow cell 1201. The adhesive seals the reference cell 1203 and the flow cell 1201 along the lap joint, such that fluid can only enter and exit through the inlet and outlet ports 1202, 1204.

The encasement is preferably formed of a material having low oxygen permeability, low moisture permeability which is transmissive to ultraviolet radiation, and which is resistant to color change upon exposure to ultraviolet radiation, such as a composition of acrylic, styrene, and butadene. Because even the preferred composition absorbs oxygen, the encasement 1200 is preferably formed with a third cell 1213. The third cell 1213 reduces the amount of encasing material which is adjacent to the flow cell 1201. However, it will be clear to those skilled in the art that such a third cell 1213 is not necessary for the proper operation of the present invention. In addition, in one embodiment of the present invention the amount of encasing material is reduced to a minimum to reduce the absorption of oxygen from a sample which is present in the flow cell 1201.

The flow cell 1201 is formed to ensure that a sample which enters the flow cell comes into contact with each of the sensors 403. Furthermore, the flow cell 1201 is very shallow, thus the volume of the flow cell 1201 is very small (i.e., 0.05 milliliters in the preferred embodiment). A very thin reference channel 1206 (preferably 0.005–0.010 inches in diameter) between the reference cell 1203 to the flow cell 1201 provides electrical contact between the reference medium which resides within the reference cell 1203. The reference medium may be any well known reference electrolyte in solution or gel form. However, in the preferred embodiment, the reference medium is preferably a natural polysaccharide, such as agarose, gelatin, or polyacrylamide. The greater viscosity of the reference medium used in the preferred embodiment retards evaporation of the reference medium, as well as preventing the reference medium from intermingling with the fluids in the flow cell 1201. The reference medium is preferably introduced into the reference cell 1203 after the sensor assembly 400 is installed in the encasement 1200. In accordance with the present invention, a vacuum is created in the flow cell 1201 and the reference cell 1203 by applying a low pressure source to either the inlet or outlet port 1204, 1206. The reference medium is then applied to the other port 1206, 1204. Preferably, the reference medium is heated to approximately 37°–50° C. by the heater 601 or by application of heat through an external heat source to reduce the viscosity of the reference medium, and thus allow the reference medium to completely fill the reference cell 1203. Once the gel has filled the reference cell 1203, any excess reference medium is gently flushed from the flow channel prior to allowing the reference medium to cool. In an alternative embodiment of the present invention, the viscosity of the reference medium may be increased in response to a chemical reaction between the medium and a catalyst which is placed into the reference channel either before or after the reference medium.

It should be noted that when the height of the fluid column over the sensor array has been minimized to conserve sample volume (0.10 inches, for example), measurement is preferably made within 10–15 seconds after the sample has entered the flow cell 1201.

It will be seen from the above description of the present invention, that the sensors are not separable into parts, but rather form a signal modular unit, designed for a predefined life, installed once, and then discarded. Discarding the unit is economically feasible due to the low cost at which such sensor assemblies can be fabricated. The present invention makes it possible to provide a low cost system which is built around standardized electronic assemblies by providing a low cost, mass producible sensor assembly that has highly accurate and reproducible results.

Figure 15A:
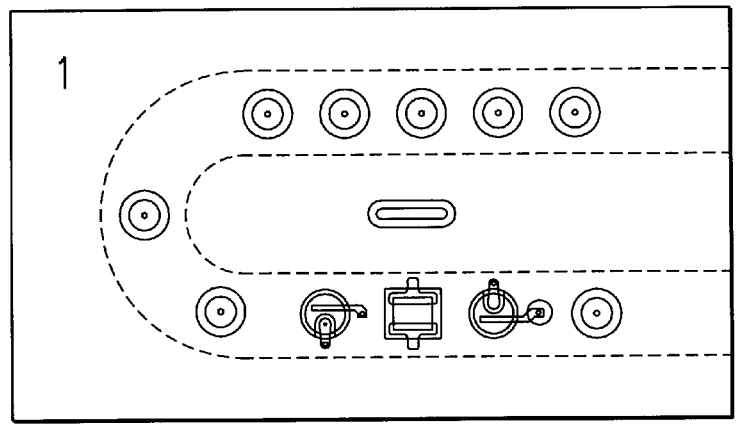
FIGS. 15a–15c illustrate alternative embodiments of the present invention in which the relative positions of the sensors differ from those shown in FIG. 4.
Figure 15B:
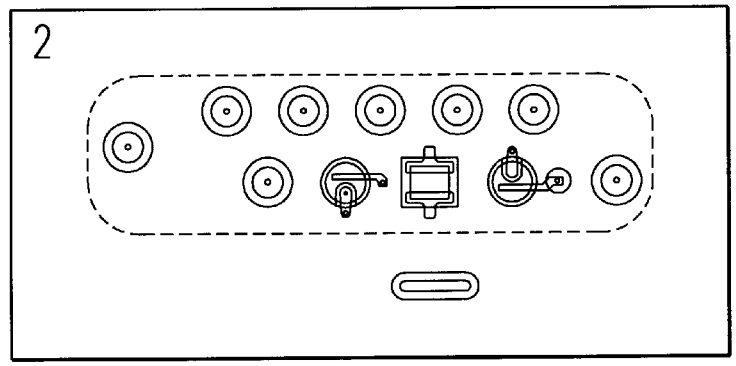
Figure 15C:
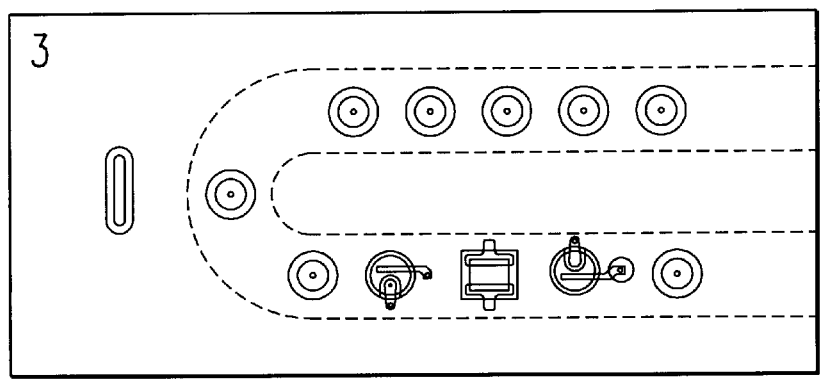

It should be clear to those skilled in the art that the use of subminiature through holes to route electrical signals from the electrodes of the sensors to the opposite side of the substrate allow a chemically selective membrane overlaying the planar electrode to function with the desired sensor reaction mechanism while providing a means for packing a number of sensors into a relatively small area on the surface of the substrate. The use of the subminiature through holes also allows for excellent physical isolation of the sample from the conductors that carry the electrical signals between the sensor electrodes and the instrumentation used to process those signals. This physical isolation results in very high electrical isolation between signals generated by each of the sensors FIGS. 15*a*–15*c* illustrate three alternative embodiments of the present invention in which the relative positions of the sensors differ from those shown in FIG. 4.

New Sensor Cartridge

Figure 16A:
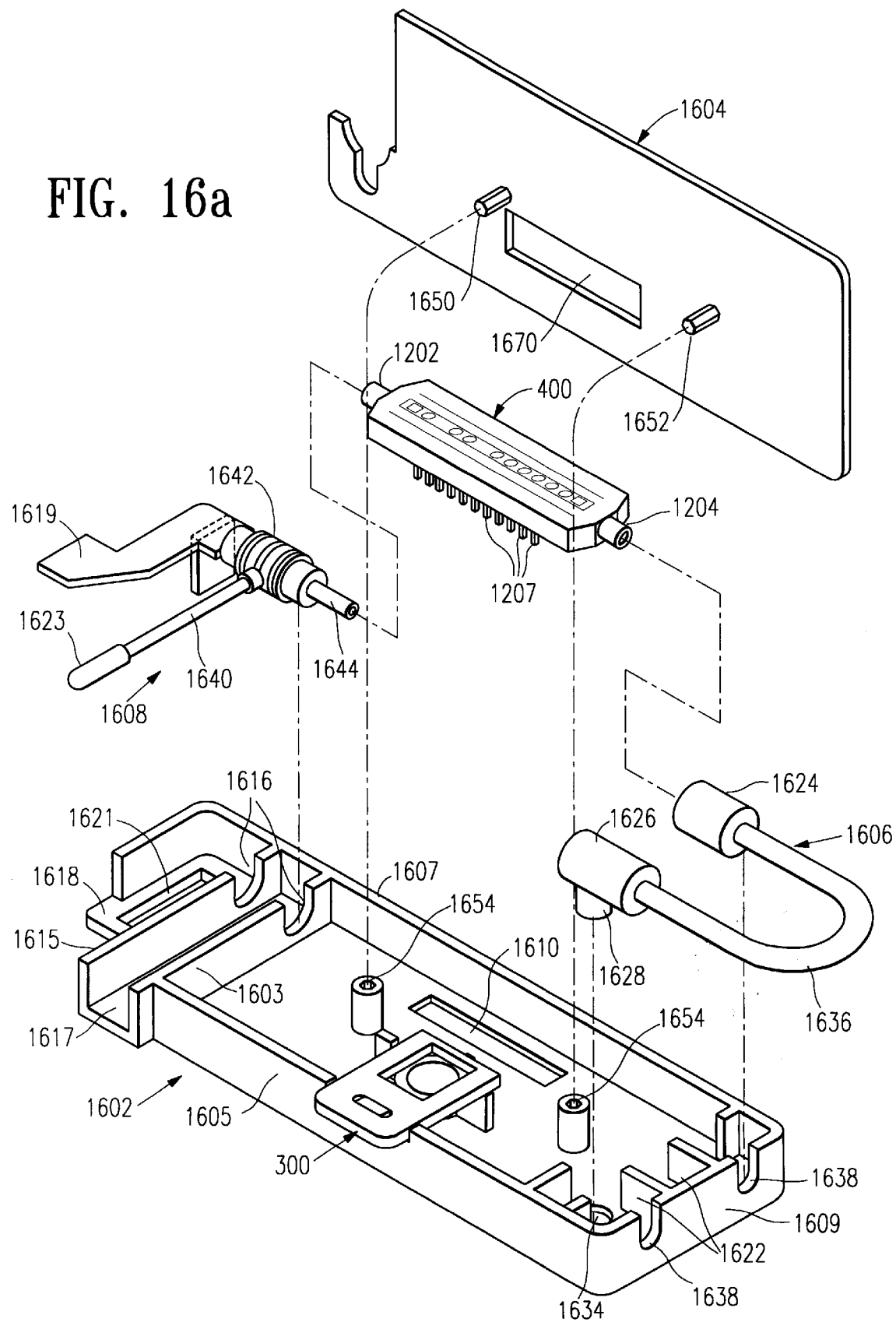
FIG. 16a is an exploded assembly view of another embodiment.

FIG. 16*a* is an assembly views of a disassembled sensor cartridge 1600 in accordance with another embodiment of the present invention. The sensor cartridge 1600 shown in FIG. 16*a* has four of the four basic component parts as in the previous embodiment; (1) a housing 1602; (2) a housing cover 1604; (3) a pump tube assembly 1606; (4), a sensor assembly 400, the same as in the prior embodiment; and (5) a novel direct input fluid aspiration port assembly 1608. This new cartridge has a direct input aspiration port 1608 wherein the fluid sample is introduced directly into the cartridge rather than routed through the analyzer as in the prior embodiment. The sensor 400 is rotated or turned around one hundred eighty degrees in the cartridge showing from its position in the prior embodiment so that the pump tube assembly 1606 is connected to the sensor outlet 1204 rather than the inlet as in the prior embodiment.

Figure 16B:
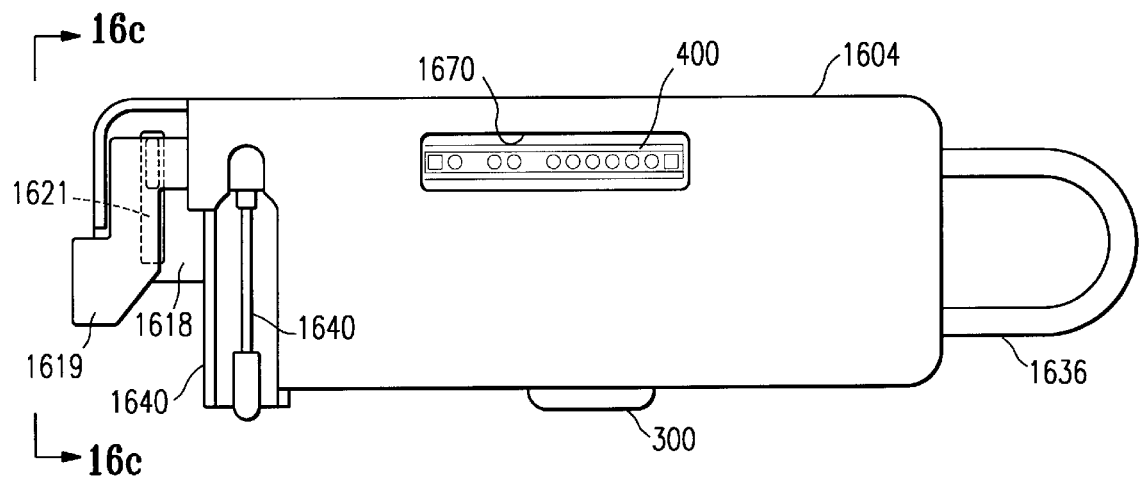
FIG. 16b is a front elevation view of the cartridge of FIG. 16a assembled X.

The housing 1602 shown in FIGS. 16*a* and 16*b* is similar in many respects to the prior embodiment and has a floor 1601, four walls 1603, 1605, 1607, 1609, an opening 1610, and in addition, a construction on one end for mounting the articulated intake aspiration stylus. Male electrical contact pins 1207 (FIG. 1*a*) of an electrical connector 1205 of the sensor assembly 400 protrude through the opening 1610. The walls of the opening 1610 generally conform to the shape and size of the body of the connector 1205 FIG. 1*b*. Thus, the sensor assembly 400 is constrained from movement in the plane of the floor 1601 of the housing 1602. Preferably, the connector body 1616 of the sensor assembly fits loosely within the opening 1610.

The pump tube assembly 1606 is substantially as in the prior embodiment and preferably comprises a right angle end fluid coupling 1626, a straight end fluid coupling 1624, and a pump tube 1636. In accordance with one embodiment of the present invention, the end fluid couplings 1624, 1626 are formed (such as by a conventional molding process) from an elastomer. The pump tube 1636 is preferably very resilient in order to allow the pump tube 1636 to exit and enter the housing at openings 1638 and properly interface with a roller to form a peristaltic roller pump, as is described below in greater detail. A fluid path is formed through the pump tube assembly 1606 such that fluid enters at one end of the pump tube assembly and exits from the other end. Walls 1622 may be provided to retain the pump tube assembly 1606 in position within the housing 1602.

Figure 16C:
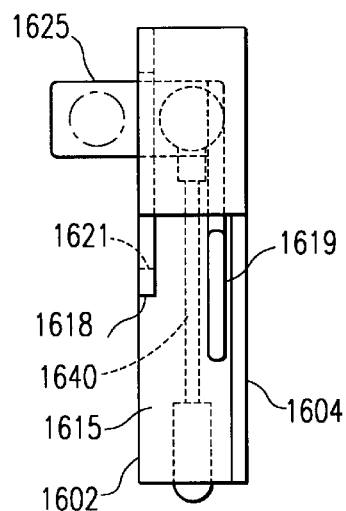
FIG. 16c is an end view of the cartridge of FIG. 16b showing the aspiration port in the setracted position X.
Figure 16D:
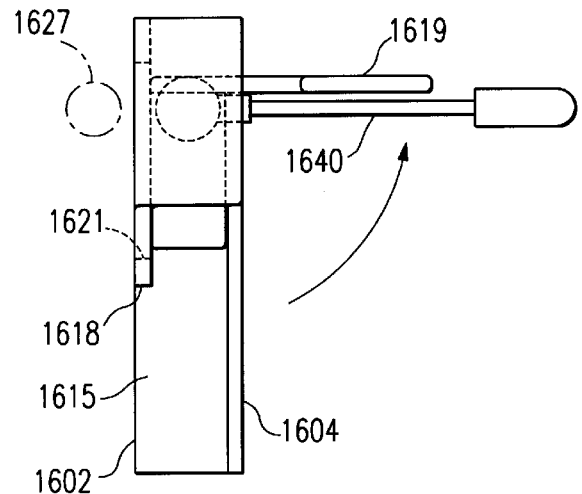
FIG. 16d is a view like FIG. 16c showing the aspiration prot in the extended position X.

The direct input aspiration port assembly 1608 includes a rotatable fluid coupling which in one embodiment comprises a tube 1640 mounted in and extends through a body 1642 and mounts in a flexible or elastomeric tube 1644 at the end of sensor assembly 400. The tube 1644 flexes to allow rotation of the tube 1640 up to about 90 degrees. The input aspiration port assembly 1608 is preferably formed as a right angle coupling with the major portion of tube 1640 at right angle to the end mounted in tube 1644 and the pivot or rotating axis. That is, the coupling provides a means by which tube 1640 rotates or pivots through about 90 degrees from a recessed positioned as shown FIG. 16*c* to a position extending outward from the surface of the housing as shown in FIG. 16*d*. The housing 1602 is provided with a wall 1615 parallel to wall 1603 and aligned openings 1616 which journal the pivoting body 1642. The parallel walls also form a recess 1617 into which the aspiration tube or stylus 1640 is normally recessed. The housing is also formed with an extension 1618 which forms a recess for an actuating lever or tab 1619 for manually rotating the aspiration tube 1640. A slot 1621 is formed in the extension 1618 to allow a tab 1625 on the back of lever 1619 to extend and retract and to activate some signal such as a switch or block a light beam to prevent operation. The tab can block a signal such as a light beam to or from a source or sensor 1627. A removable protective elastomeric cap 1623 covers the inlet end of tube 1644. In accordance with one embodiment of the present invention, port 1204 of the sensor assembly is directly coupled to the pump tube assembly 1606. The inlet port 1202 of the sensor assembly 400 is coupled to the input aspiration port assembly 1608. The cover 1604 is preferably translucent or clear and has a transparent window to enable viewing of the sensors. Furthermore, as will be described in greater detail below, a plastic encasement 1200 (see FIG. 14) is also preferably either translucent or clear. Since the cover and the plastic encasement are either translucent or clear, the user can view the movement of analytes gas bubbles, and reagents through the sensor assembly within the cartridge. In accordance with one embodiment of the present invention, illustrated in FIG. 16*b*, the cover 1604 has an opening 1670 which allows the user of a blood analyzer into which the cartridge is to be installed to view the sensor assembly directly. Accordingly, the user may directly observe an analyte gas bubbles and reagents flowing through the sensor assembly.

Two reinforced holes 1650, 1652 are provided through the cover 1604. The holes 1650,1652 align with two hollow generally cylindrical bosses 1654 which extend up from the floor 1601 of the housing 1602 to accept retaining devices, such as screws, which secure the cover 1604 to the housing 1602. In an alternative embodiment of the present invention, studs extend from the cover in alignment with the bosses 1654. Each stud fits tightly within the opening in one of the bosses 1654 in order to secure the cover 1604 to the floor 1601 of housing 1602.

In accordance with one embodiment of the present invention, the cartridge of the present invention is assembled by coupling the input aspiration port assembly or inlet 1608 to a first port 1202 of the sensor assembly 400. The fluid coupling 1624 is coupled to the other port 1204 of the sensor assembly 400. The combination of input aspiration port assembly 1608, sensor assembly 400, and pump tube assembly 1606 are then lowered into the housing 1602 and the protrusion 1628 is inserted into the opening 1634. The pump tube 1636 is inserted into openings 1638 in the wall 1609 of the housing 1602. A latch member 300 is also provided and mounted in the housing as in the FIG. 3 embodiment. The cover 1604 is then placed over, and secured to, the housing 1602.

Figure 17:
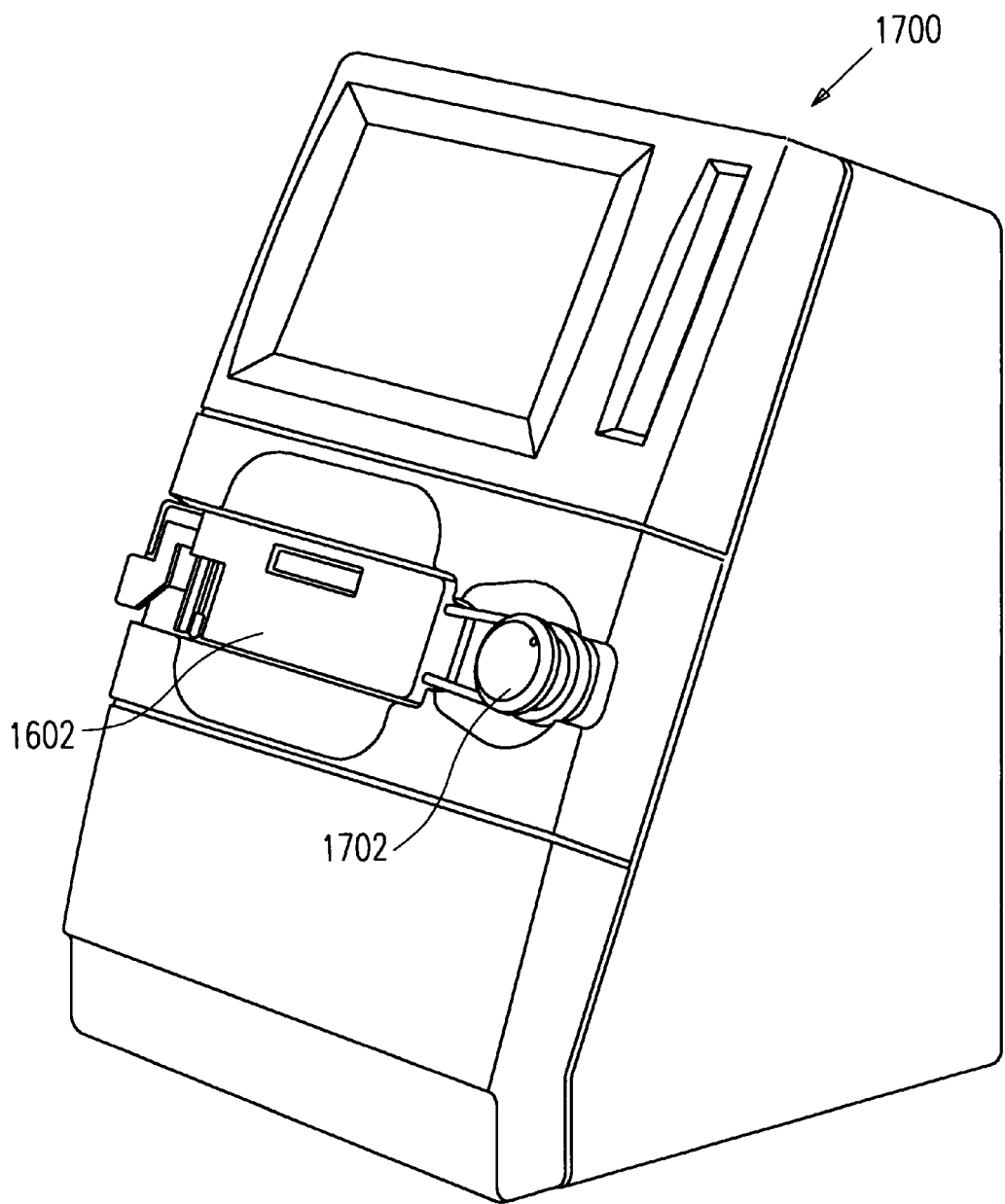
FIG. 17 is a perpective view of a blood analyzer in accordance with a further embodiment of the invention.

Once the cartridge 1600 is assembled, it may be installed in a blood analyzer, such as the blood analyzer 1700 illustrated in FIG. 17. The blood analyzer of the present invention has a fluid connector (not shown, but like connectors 202 and 204 of FIG. 2*a* and 2*b*) for connection to port 1626 on the cartridge. The direct input aspiration port assembly 1608 provides a fluid flow path via inlet 1202 into cartridge sensor housing 400. The fluid flow path continues through the cartridge sensor housing via outlet 1404, through the pump tube assembly 1606, through the right angle end fluid coupling 1626 and via the male fluid connector which mates with the fluid coupling 1626 to complete a fluid flow path into the analyzer.

Fluids are pumped along the fluid flow path by a peristaltic roller pump which includes a roller 1702 that massages the pump tube 1636. That is, the pump tube 1636 is preferably resilient enough to be stretched over the roller 1636. The roller 1702 applies areas of alternating greater and lesser pressure to the pump tube 1636, causing those portions of the pump tube 1636 that lie over an area of greater pressure to be internally constricted and those areas of the pump tube 1636 that lie over an area of lesser pressure to be relaxed to essentially the full unstressed diameter of the channel through the interior of the pump tube 1636. As the roller 1702 rotates, the areas of alternating greater and lesser pressure traverse the pump tube to generate a peristaltic action in the pump tube 1636.

It can be seen from the above description of the disposable cartridge that the present invention provides a cartridge that: (1) is very easy to install, and thus may be installed with virtually no training; (2) establishes both electrical and fluid connections in one installation process with little or no risk of misaligning the electrical or fluid connections of the cartridge with the corresponding connections of the blood analyzer; (3) includes an integral inexpensive and reliable pump tube assembly; (4) allows the user of the blood analyzer to see the movement of an analyte, gas bubbles, or reagent during analysis; (5) is inexpensive and thus may be disposed of without concern for excessive cost; (6) facilitates rapid, reliable replacement of the sensors of the blood analyzer; (7) reduces contact between blood elements and the analyzer; (8) is compact in size; (9) can be used for sensors with different analyte panels; and (10) allows one type of analyzer to accept many different types of sensors.

It should be understood that the cartridge of the present invention may be provided in numerous alternative configurations. For example, a plurality of sensor assemblies may be coupled in series to provide redundancy or to increase the number or type of sensors that are provided within the cartridge. Furthermore, straight fluid couplings may replace the right angle fluid couplings, and flexible tubing may be used to alter the direction of the flow path. Furthermore, the pump tubing may be directly coupled to the sensor assembly without the need for a fluid coupling between the pump tubing and the sensor assembly. Furthermore, a wide variety of latching mechanisms may be used to securely latch the cartridge to a blood analyzer.

SUMMARY

A number of embodiments of the present invention have been described. Nevertheless, it will be understood that various modifications may be made without departing from the spirit and scope of the invention. For example, while the present invention is described generally as being fabricated using a thick film technique, any other well known layered circuit technique may be used, such as thin film, plating pressurized laminating, and photolithographic etching. Furthermore, substrates for a number of sensor assemblies may be fabricated concurrently on a single section of ceramic material which has preferably been scored to allow for easy separation into individual substrates after deposition of all of the components of the sensor assembly, and prior to installation in an encasement. Accordingly, it is to be understood that the invention is not to be limited by the specific illustrated embodiment, but only by the scope of the appended claims

What is claimed is:

1. A blood analyzer sensor cartridge comprising:
a housing having means defining a chamber and a sensor assembly within the chamber;
an elongated tubular member pivotally mounted to said housing defining a first fluid port adapted for insertion in a sample container for direct introduction of a sample into said chamber;
first fluid path means in said housing communicating said first fluid port with said sensor assembly;
a second fluid port in said housing adapted for connection to an analyzer; and
second fluid path means in said housing communicating said sensor assembly with said second fluid port.

2. The cartridge of claim 1, wherein the mechanical mating of the cartridge to an analyzer is accomplished by movement of the cartridge in a straight line toward the analyzer.

3. The cartridge of claim 1, wherein the housing has an opening and the sensor assembly includes an electrical connector which protrudes through the opening in the housing.

4. The cartridge of claim 3, wherein the sensor assembly includes a flow path and a pump tube assembly, the pump tube assembly includes: (1) a flow path therethrough; (2) a first end coupling for placing the flow path through the pump tube assembly in fluid communication with the sensor assembly flow path; and (3) a pump tube for mechanically interfacing with a pump in order to create a peristaltic pumping action within the pump tube.

5. The cartridge of claim 4, wherein said tubular member is an aspiration tube that is rigid and is connected by an elastomeric tube coupling to said sensor assembly.

6. A blood analyzer sensor cartridge comprising:
a housing having means defining a chamber and a sensor assembly within the chamber;
a member defining a first fluid port adapted for insertion in a sample container for direct introduction of a sample into said chamber;
first fluid path means in said housing communicating said first fluid port with said sensor assembly;
a second fluid port in said housing adapted for connection to an analyzer; and second fluid path means in said housing communicating said sensor assembly with said second fluid port, wherein said member defining said first fluid port comprises an elongated aspiration tube pivotally mounted to said housing for selective orientation within a range of up to ninety degrees.

7. The cartridge of claim 6, wherein said aspiration tube is moveable from a protective recess in said housing to a position normal to a face of said housing.

8. The cartridge of claim 7, wherein said aspiration tube comprises a lever for moving said aspiration tube to and from said recess.

9. The cartridge of claim 8, wherein said second fluid path means comprises a pump tube assembly.

10. The cartridge of claim 9, wherein the pump tube assembly includes an elastomeric tube which mechanically interfaces with a pump roller in order to create a peristaltic pumping action within the pump tube, the sensor assembly includes a flow path; and the pump tube assembly includes: (1) a flow path through the pump tube; and (2) a first end coupled to said sensor assembly and a second end coupled to said second fluid port for placing the flow path through the pump tube assembly in fluid communication with the flow path through the sensor assembly.

11. The cartridge of claim 10, wherein the pump tube assembly further comprising an end coupling, the end coupling being coupled between the second end of the pump tube assembly and the second housing fluid port at a right angle with respect to the longitudinal axis of the pump tube.

12. The cartridge of claim 7, further comprising:
an electrical connector having electrical contacts; and
an end coupling, the end coupling being coupled between an
end of the pump tube assembly and the second housing fluid port; wherein the end coupling protrudes beyond the housing at least as far as the electrical contacts of the connector to guide the electrical contacts into proper alignment with mating contacts of the analyzer as the cartridge is installed on the analyzer.

13. The cartridge of claim 6, wherein said aspiration tube is moveable from a generally vertical downward position to a generally horizontal position.

14. The cartridge of claim 13, further comprising a lever for moving said aspiration tube between said downward position and said horizontal position.

15. The cartridge of claim 14, wherein said lever includes a tab for activating a sensor.

16. The cartridge of claim 14, wherein said lever extends and retracts through an opening in said housing.

17. The cartridge of claim 6, wherein the sensor assembly has a cover and the cover has an opening through which analyte may be viewed in the sensor assembly during analysis.

18. A blood analyzer sensor cartridge comprising:
a housing having chamber and a sensor assembly within the chamber;
an elongated tubular member pivotly mounted to said housing and defining a first fluid port adapted for insertion into a sample container for direct introduction of a sample into said housing;
a first fluid path in said housing communicating said first fluid port with said sensor assembly;
a second fluid port in said housing adapted for connection to an analyzer; and
a pump tube defining a second fluid path communicating said sensor assembly with said second fluid port.

19. The cartridge of claim 18, wherein said tubular member defining said first fluid port comprises an elongated aspiration tube pivotally mounted to said housing for selective orientation within a range of up to ninety degrees between a substantially vertical orientation and a substantially horizontal orientation.

20. The cartridge of claim 19, wherein said aspiration tube is moveable from a protective recess in said housing to a position normal to a face of said housing.

* * * * *